United States Patent [19]
Vollmann et al.

[11] Patent Number: 4,561,442
[45] Date of Patent: Dec. 31, 1985

[54] IMPLANTABLE CARDIAC PACER WITH DISCONTINUOUS MICROPROCESSOR PROGRAMMABLE ANTITACHYCARDIA MECHANISMS AND PATIENT DATA TELEMETRY

[75] Inventors: William Vollmann, N. Lauderdale; Van E. Mumford, Miami, both of Fla.

[73] Assignee: Cordis Corporation, Miami, Fla.

[21] Appl. No.: 542,889

[22] Filed: Oct. 17, 1983

[51] Int. Cl.$^4$ ............................................. A61N 1/36
[52] U.S. Cl. .............................................. 128/419 PG
[58] Field of Search ................................. 128/419 PG

[56] References Cited

U.S. PATENT DOCUMENTS 4,390,022  6/1983  Caltee et al. ................. 128/419 PG

FOREIGN PATENT DOCUMENTS 77845  5/1983  European Pat. Off. ...... 128/419 PG
2492552  4/1982  France ......................... 128/419 PG Primary Examiner—William E. Kamm
Attorney, Agent, or Firm—Henry W. Collins; George H. Gerstman

[57] ABSTRACT

A multi-programmable ROM-less cardiac pacer employs an intermittent microprocessor turned ON and OFF by a pacer timer clockwise independent of the processor to time intervals preset by the processor. Sensed activity and external communications restart the processor with an interrupt request. Five antitachycardia mechanisms are externally programmable: programmed burst, burst rate scanning, automatic overdrive, programmed critically timed and critically timed scanning. In scanning mechanisms, the interval changes progressively until the tachycardia is terminated by a successful interval which is stored. Runaway protection is executed in the software. For telemetry, the pacer collects the following monitored pacing data over a programmable period of time: percent pacing, average rate, maximum rate, number of tachycardia episodes and maximum tachycardia duration.

13 Claims, 27 Drawing Figures

Microfiche Appendix Included
(2 Microfiche, 83 Pages)

ORTHOCOR II
FUNCTIONAL BLOCK DIAGRAM

MICROPROCESSOR
TIMING CYCLE

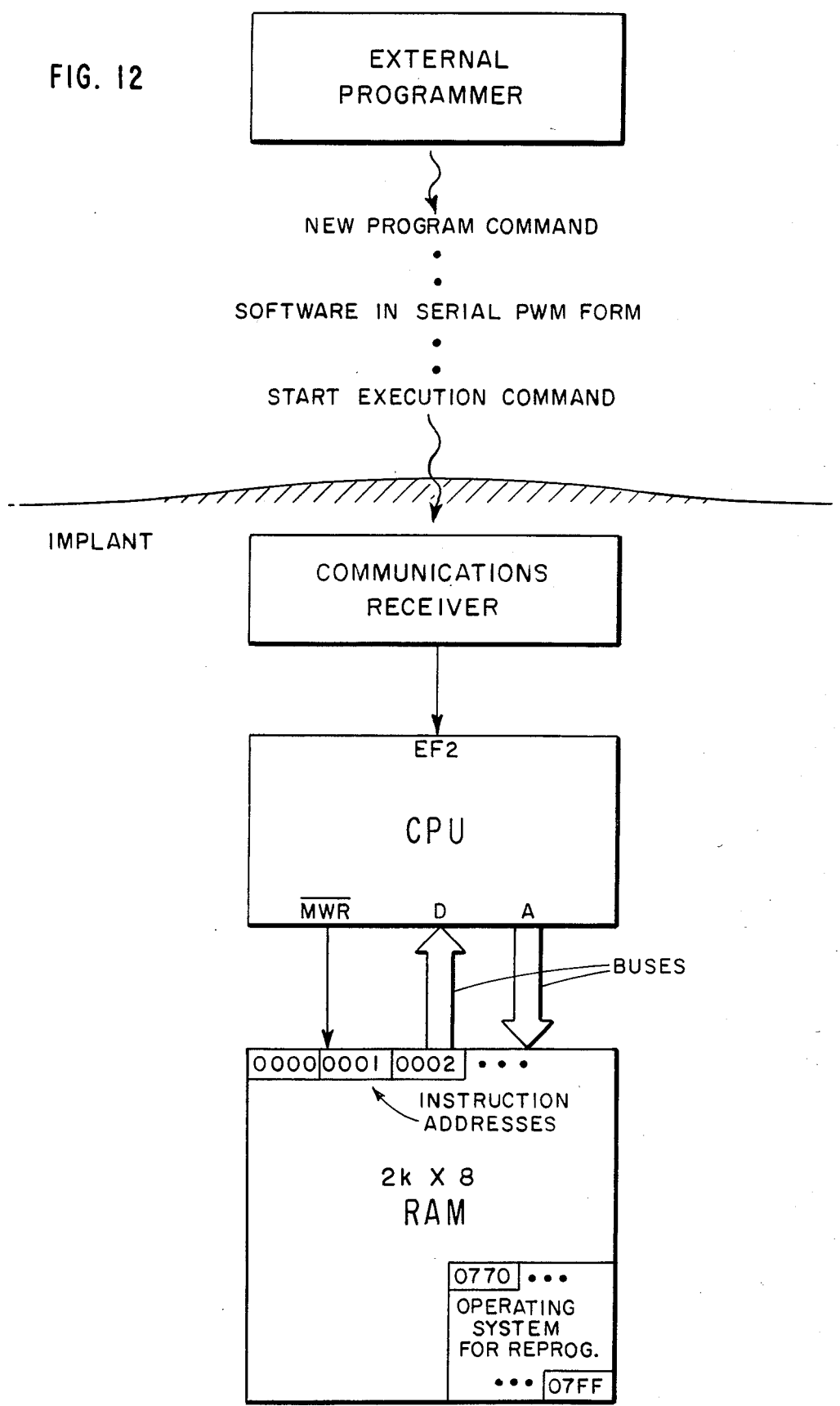

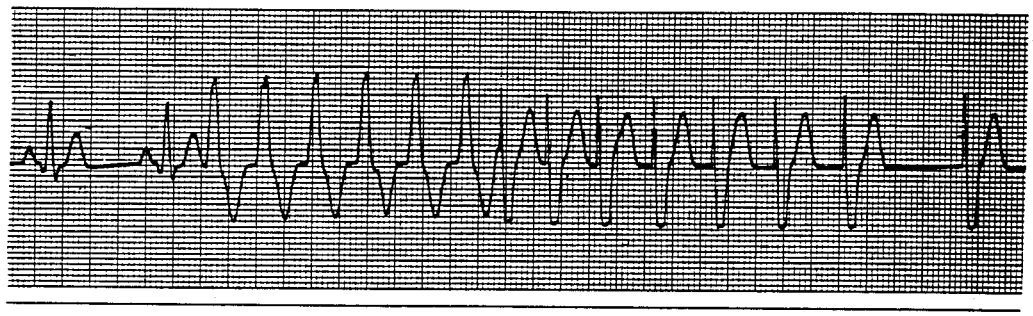
6 INTERVALS LESS THEN 600 msec   BURST SEQUENCE-7 PULSES   FIG. 13
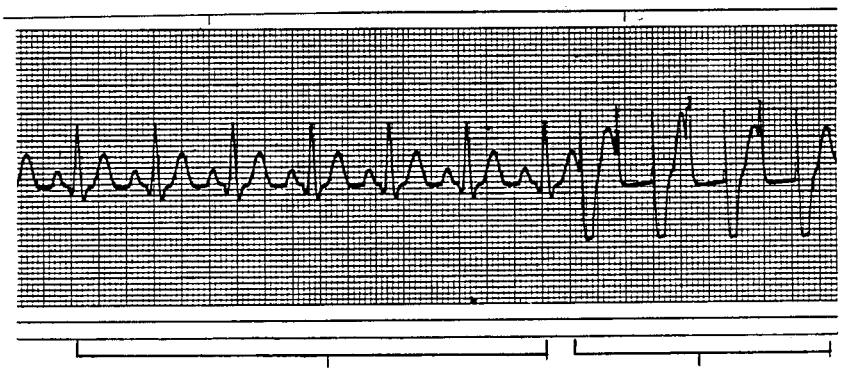
6 INTERVALS LESS THAN 600 msec   FIRST BURST SEQUENCE
7 PULSES AT 230 ppm
FIG. 14
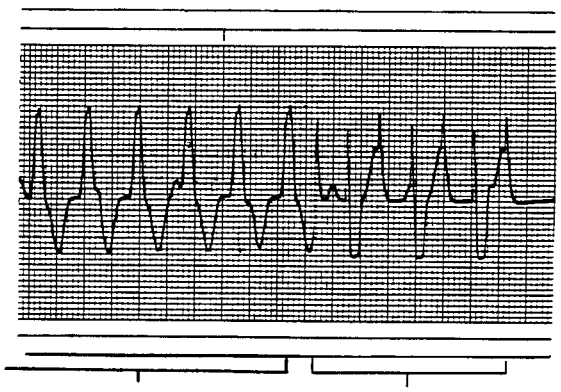
TACHYCARDIA STILL PRESENT,   SECOND BURST SEQUENCE
6 INTERVALS LESS THAN 600 msec   7 PULSES AT 262 ppm
(INTERVAL DECREASED
BY SCAN DELTA)

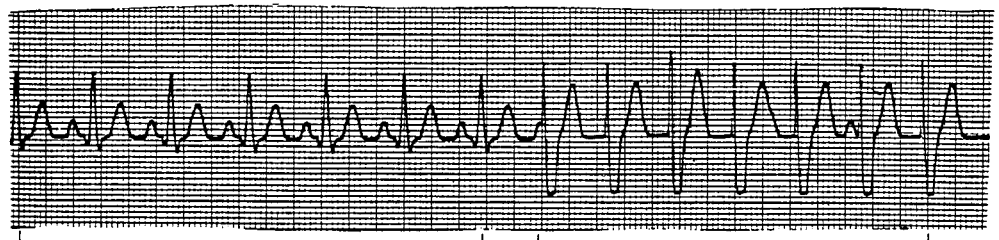
6 INTERVALS LESS THAN 600 msec
MEASURE INTERVALS TO BE
560 msec
FIG. 15 OVERDRIVE SEQUENCE, (MEASURED INTERVALS 7 PULSES AT 130 ppm OVERDRIVE CONSTANT)
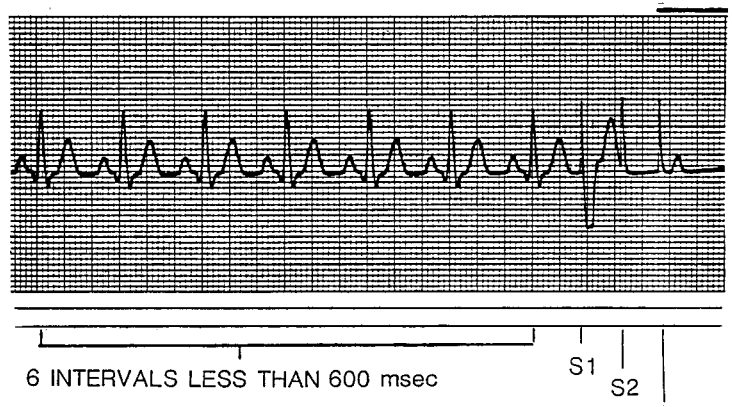
6 INTERVALS LESS THAN 600 msec      S1  S2  S3
FIG. 16
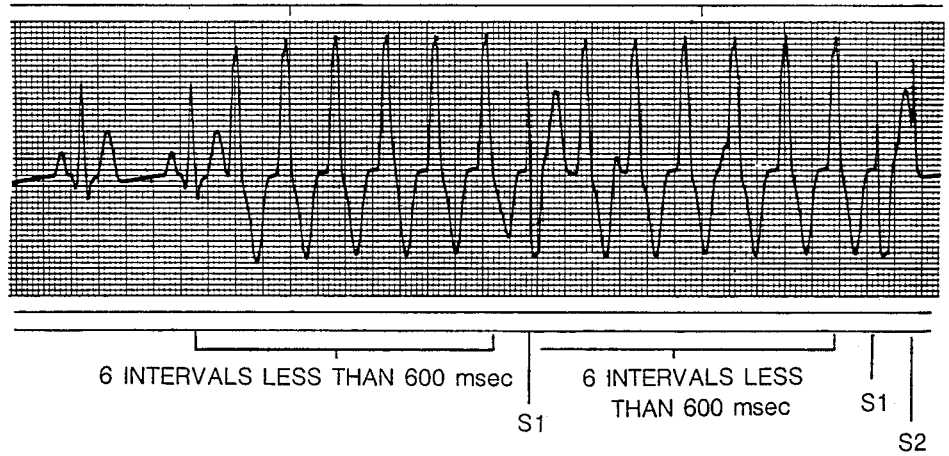
6 INTERVALS LESS THAN 600 msec | 6 INTERVALS LESS THAN 600 msec
S1                                                    S1  S2
FIG. 17

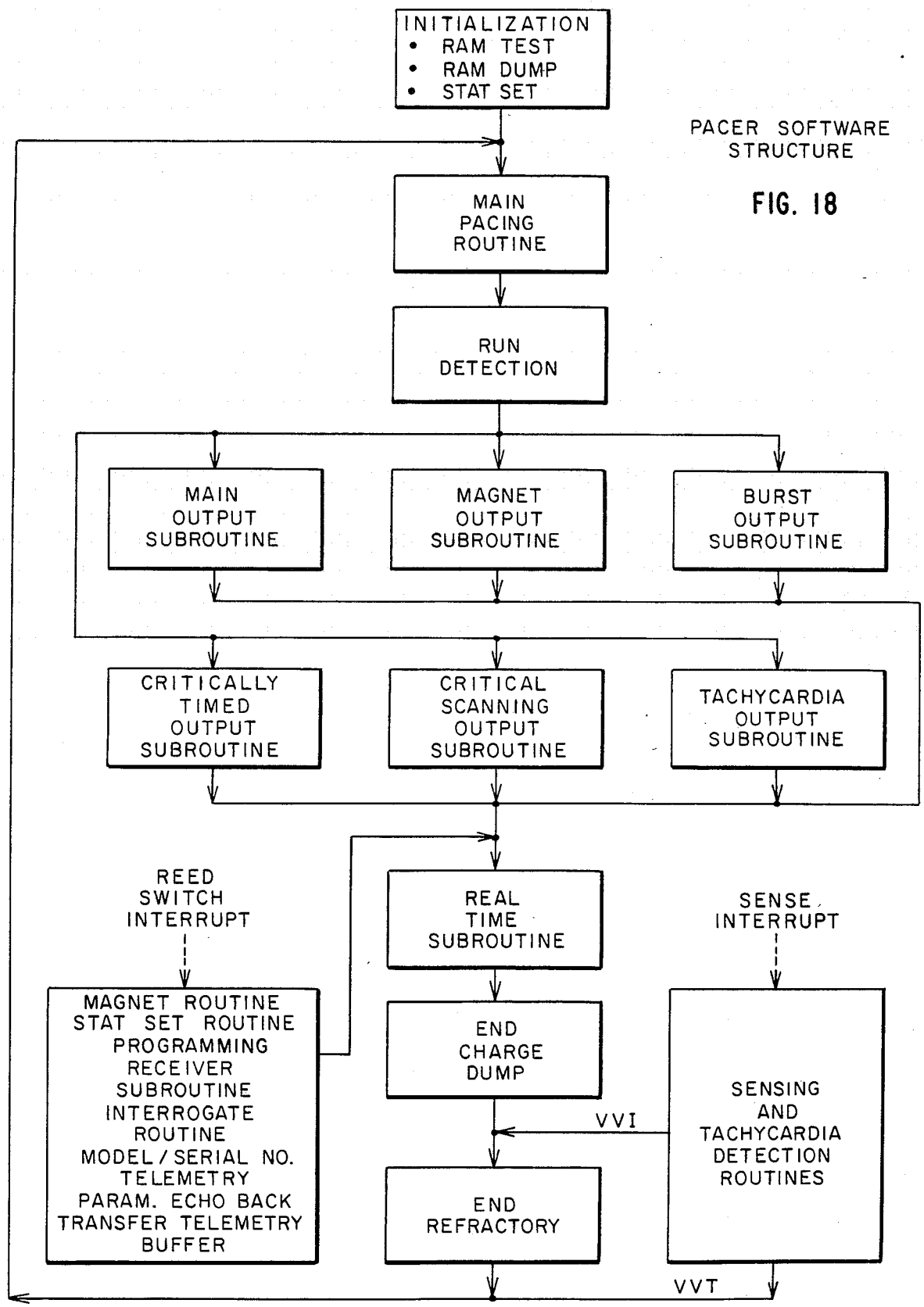

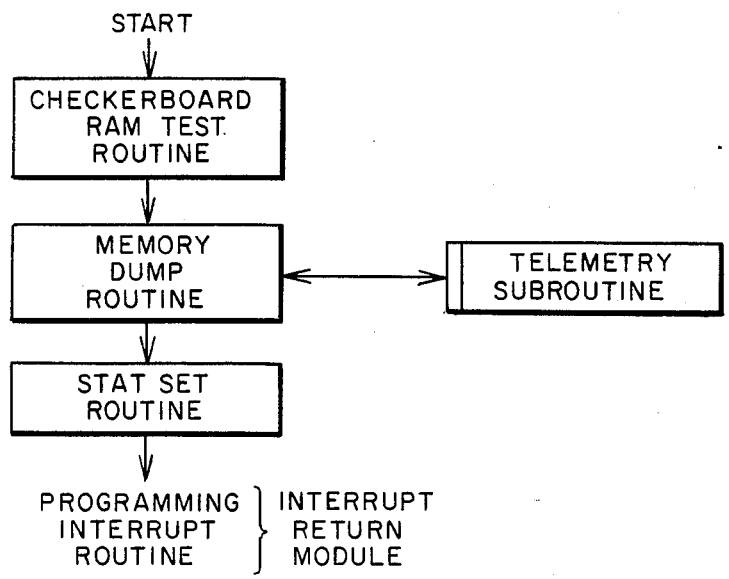
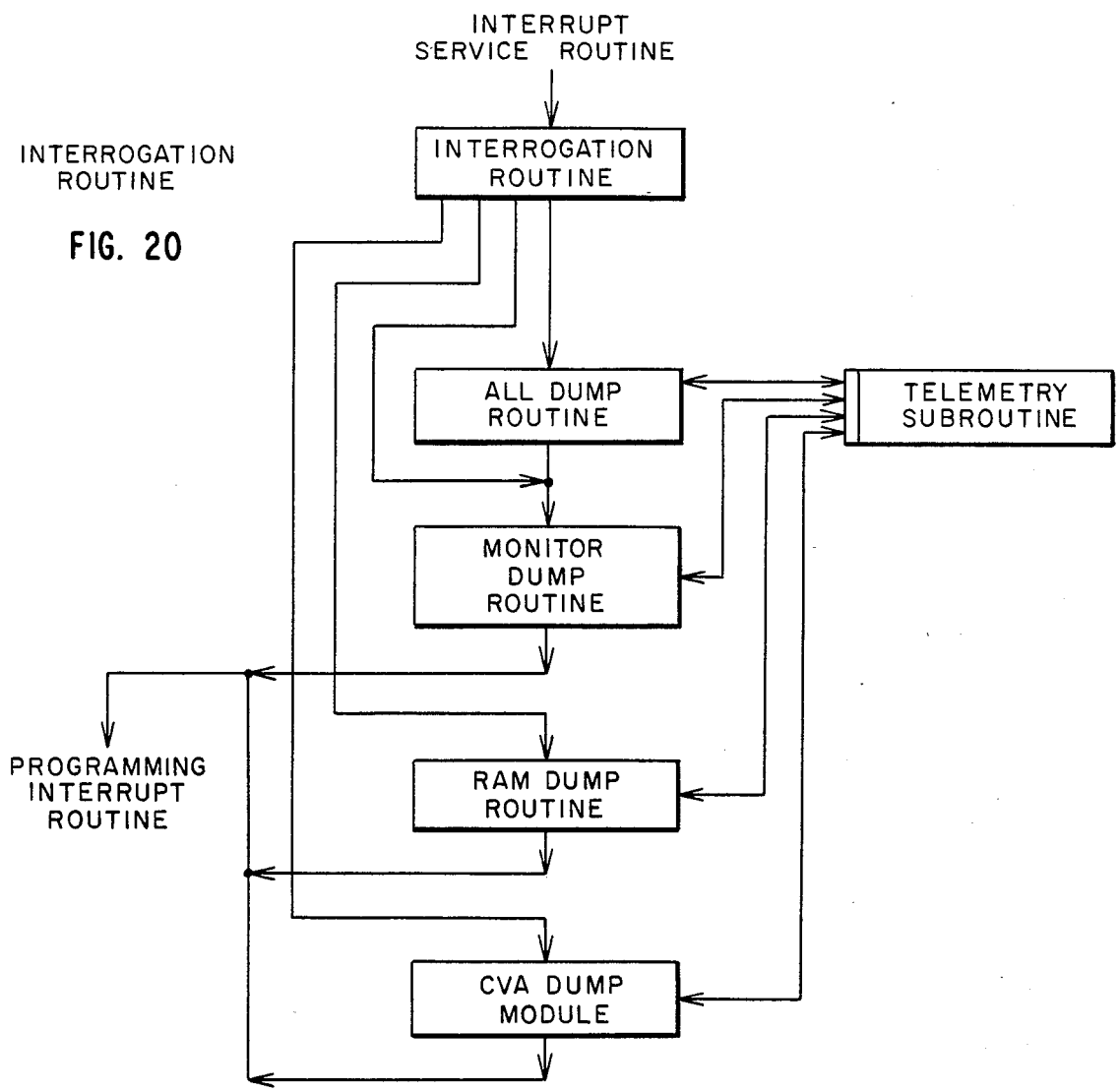

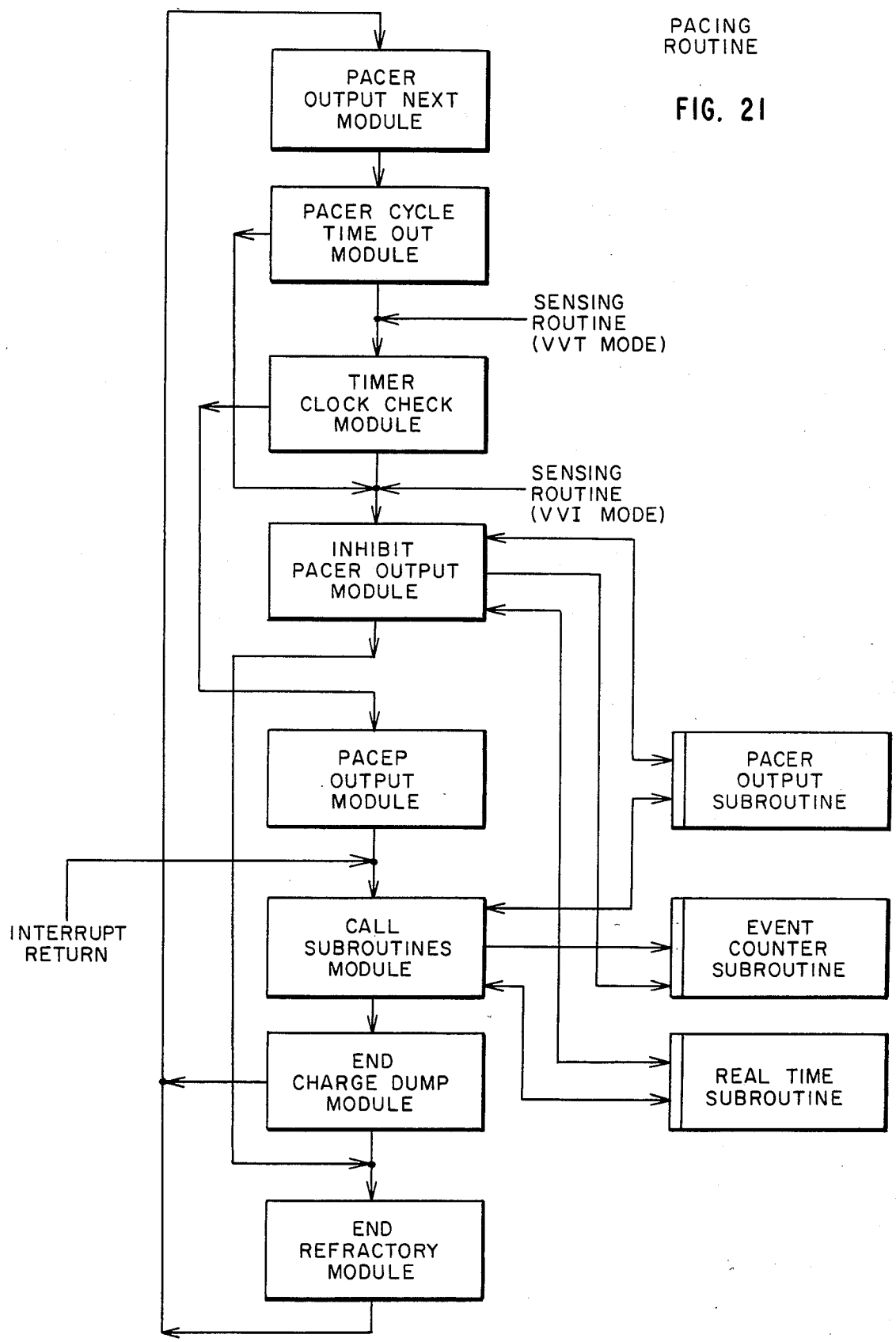

PACER OUTPUT SUBROUTINES

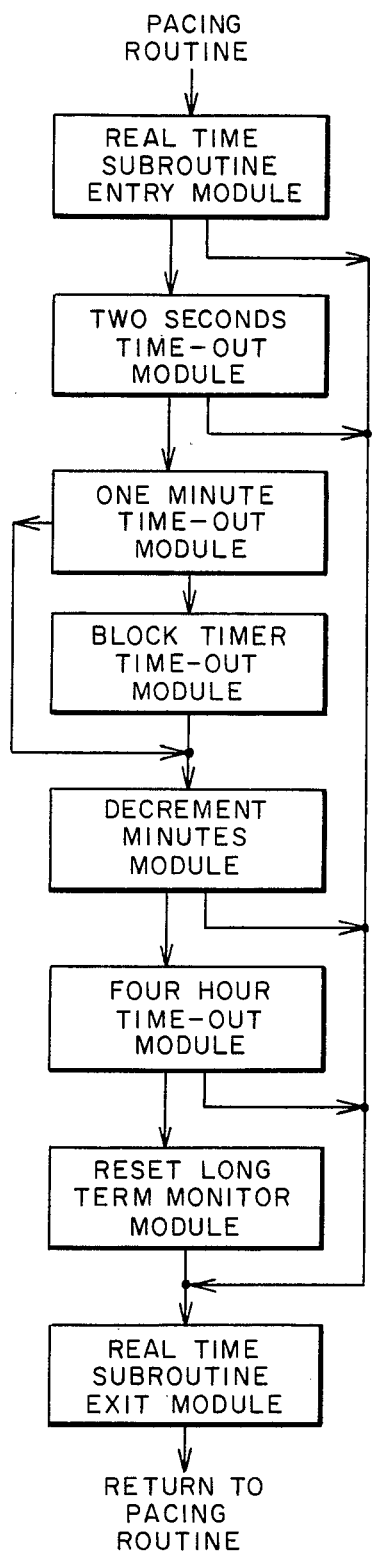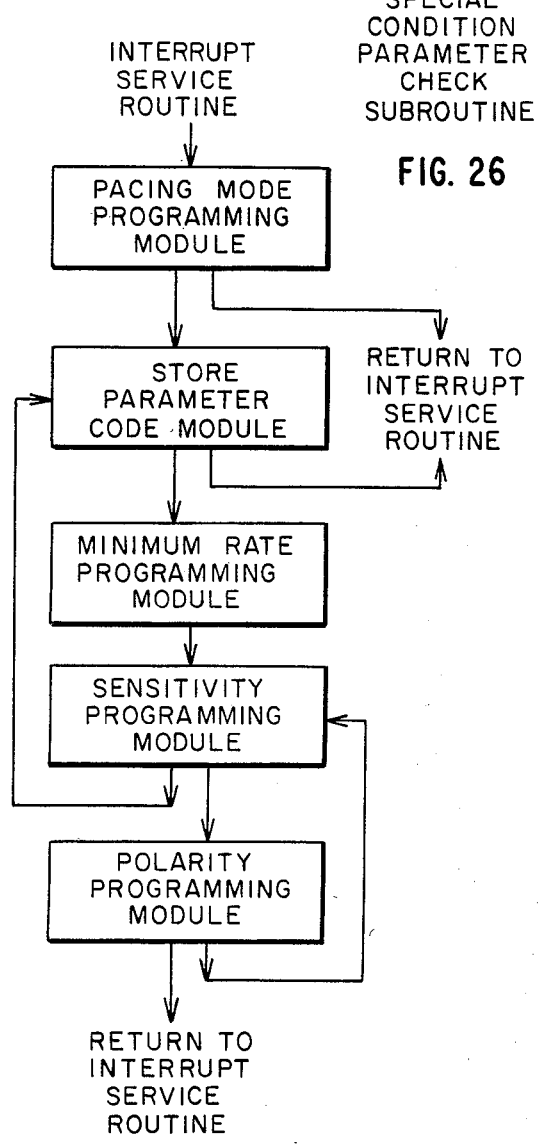

4,561,442

IMPLANTABLE CARDIAC PACER WITH DISCONTINUOUS MICROPROCESSOR PROGRAMMABLE ANTITACHYCARDIA MECHANISMS AND PATIENT DATA TELEMETRY

REFERENCE TO MICROFICHE APPENDIX

Incorporated herein by reference is a microfiche appendix consisting of two microfiches containing 83 pages of annotated microprocessor instruction listings.

BACKGROUND OF THE INVENTION

The invention relates generally to implantable biological tissue stimulators, and the specific embodiment relates particularly to advanced implantable cardiac pacers employing microcomputer technology, telemetry and antitachycardia systems.

The major pumping chambers in the human heart are the left and right ventricles. Simultaneously contracting these chambers expel blood into the aorta and the pulmonary artery. Blood enters the ventricles from smaller antechambers called the left and right atria which contract about 100 milliseconds (ms) before the ventricles. This interval is known as the atrioventricular (AV) delay. The contractions are induced by a wave of spontaneous electrical excitation which begins in the right atrium, spreads to the left atrium and then enters the AV node which delays its passage to the ventricles via the so-called bundle of His. The frequency of the waves of excitation is normally regulated metabolically by the sinus node. The atrial rate is thus referred to as the sinus rate or sinus rhythm of the heart.

Electrical signals corresponding to the contractions appear in the patient's electrocardiogram. A brief low amplitude signal known as the P-wave accompanies atrial contraction, normally followed by a much larger amplitude signal, known as the QRS complex, with a predominant R-wave signifying ventricular contraction. Repolarization prior to the next contraction is marked by a broad waveform in the electrocardiogram known as the T-wave.

A typical implanted cardiac pacer operates by supplying missing stimulation pulses on a pacing lead attached to the ventricle. The electrical stimulus independently initiates contraction. The R-wave can be sensed by the same lead and used as a timing signal to synchronize or inhibit stimulation pulses in relation to spontaneous cardiac activity. The atrium also can be sensed and/or stimulated by a separate lead lying in the atrial appendage. In AV sequential pacers both atrial and ventricular leads are used for sequential stimulation of the atrial and ventricular chambers. An example is shown in U.S. patent application Ser. No. 207,003 entitled "Multi-Mode Microprocessor-Based Programmable Cardiac Pacer", filed Nov. 14, 1980 by Leckrone et al, (hereinafter referred to as the 207,003 application), assigned to the assignee of the present application.

Although usually only supplementing cardiac function, cardiac pacers can be life supporting devices. They are surgically implanted and remain inside the patient's body for many years. Malfunctions are rare but the mere possibility of requiring surgical replacement dictates a conservative approach, if not reluctance, toward exploiting new developments in electronic circuitry. In the past, the relatively straightforward functional requirements were successfully implemented even with analog hardware circuit configurations.

The state of the art in compact batteries has also been a major factor. Current drain must be minimized to avoid unnecessary surgical replacements and reprogramming of an expensive new pacer.

Reliability is the chief concern, however, followed closely by low current drain and compactness. Driven largely by the latter concerns, the industry gradually moved to adopt low power digital integrated circuits and, most recently, microprocessors. Examples of microprocessor-based pacers are contained in the 207,003 application, U.S. patent application Ser. No. 430,507, entitled "Multi-Mode Microprocessor-Based Programmable Cardiac Pacer" filed Sept. 30, 1982 by William Vollmann and U.S. patent application Ser. No. 195,665 filed Oct. 9, 1980 by Alan Lesnick, entitled "Implantable Externally Programmable Microprocessor-Controlled Tissue Stimulator", all three assigned to the assignee of the present application. Microprocessor technology presents the challenge of writing a pacing routine which monitors sense amplifier outputs indicative of spontaneous activity of the heart and safely determines and provides the type of stimulation that would be best suited to a given condition. The main problem in exploiting this technology is safety. To be sure, the boundless complexities of computer programming give rise to new opportunities for versatility. However, residual design faults all too often exist as evidence of the designer's inadequate mastery of the complexity of their system.

The interest in microprocessors for tissue stimulators intensified following the introduction of the first low power CMOS single chip microprocessors. One of the first complete implementations is documented in the 195,665 application in which a microprocessor is used in a neural stimulator for alternating lead connections and reprogramming stimulation parameters. In this configuration, a separate timer is employed to time fixed stimulation pulse intervals. Meanwhile, a slow CPU clock keeps the microprocessor running to respond to interrupts. When the timer times out, a fast CPU clock is substituted to manipulate the lead configuration. In contrast, the computer-based pacers of the 207,003 and 430,507 applications depend on software execution for interval timing. A standard scan cycle (14 ms) is established in the pacing routines. No matter what sequence of decisions and actions are taken, the pacing routine scan cycle always consumes the same number of machine cycles. Tailoring every possible software path through the pacing routine to the same number of machine cycles requires wasteful delay loops and a less than optimum clock rate.

Among the variety of cardiac symptoms encountered by cardiologists, one of the most complex is tachyarrhythmia. In atrial tachycardia, for example, the sinus rate accelerates uncontrollably to 180 to 300 beats per minute (bpm). Atrial tachycardia response modes are disclosed in the 207,003 and 430,507 applications. In the fallback mode, the pacer rate is increased to a point just below the maximum rate. Every few seconds the rate is decreased by 1 scan cycle (14 ms) until it reaches the programmed fallback rate. A programmable option is 2:1 AV block at atrial rates greater than the maximum rate which is set equal to the atrial refractory period. These systems do not attempt to break or interfere with the patient's tachycardia.

Overdrive pacing systems requiring external intervention have been used to attempt to break tachycardias. See, for example, U.S. patent application Ser. No. 243,135 entitled "Cardiac Pacer Apparatus" filed Mar. 12, 1981 by Peter Tarjan assigned to the assignee of the present application. Systems of this kind are called antitachycardia mechanisms to differentiate them from mere tachycardia response modes.

Noninvasively programmable cardiac pacers have become widely accepted over the past ten years and are now considered a necessity in most applications. RF or magnetic impulse transmission allows an external programmer to enter new pacing parameter data in the pacer's registers by coded transmissions. More recently, outbound telemetry systems have been devised to allow the implant to retransmit parameter information to the outside programmer to report the current parameters and confirm reprogramming. Expanding outbound telemetry to include patient data is another one of the subjects of the present invention.

SUMMARY OF THE INVENTION

One of the objectives of the invention is to realize software control of all pacer functions while lowering power consumption.

Another object of the invention is to stop tachycardia in the atria or ventricles automatically by means of versatile computer software embedded in the patient.

A further object of the invention is to telemeter out patient data collected, assembled and stored by the pacer itself, along with messages previously entered by the physician.

These and other objects of the invention are achieved by a multi-programmable cardiac pacer with a discontinuous microprocessor, or programmable plurality of automatic antitachycardia mechanisms and a patient monitor for short term data as well as cumulative data collected by the pacer. In the preferred embodiment a single channel ROM-less pacer is controlled by factory loadable software stored in a random access memory (RAM) executed by a low power microprocessor driven by a high speed clock gated by a timer circuit clockwise independent of the microprocessor in a semi custom low power universal array microcomputer peripheral (LUMP). The microprocessor is turned ON intermittently by enabling the CPU clock only three times during a normal pacer cycle. The frequency dependent microprocessor functional current drain is thus minimized. In the event of an interrupt due to spontaneous sensed cardiac activity or an external communication, the microprocessor will "wake up". After performing its next prescribed task, the microprocessor will in effect "go back to sleep" by disabling its own clock input. Before doing so, however, it computes a default sleep time interval and enters the proper binary number into the timer circuit. If an interrupt does not occur within the sleep time interval, the timer times out, disables interrupt capability and the microprocessor is turned back ON, for example, to enable the sense amplifier or to issue a stimulation output pulse.

In the preferred embodiment, the LUMP circuit is a single chip standard gate array masked to furnish clock circuits, a hardware pacer timer, input/output transmission gates for loading the RAM and interfacing in the computer buses, interrupt logic, and microprocessor clock control. The LUMP circuit, microprocessor and RAM comprise a 3-chip digital hybrid circuit.

Five separate automatic antitachycardia mechanisms can be externally programmed: programmed burst, burst rate scanning, automatic overdrive, programmed critically timed and critically timed scanning. In the scanning embodiments, the relevant interval changes progressively until the tachycardia is terminated. The system remembers the successful interval. The tachycardia threshold rate governing access to the programmed antitachycardia mechanism is also programmable along with the maximum number of termination attempts. In automatic overdrive a burst of pulses is applied at a rate faster by a programmable amount than the running average intrinsic rate.

The preferred embodiment provides for telemetry of programmed parameters, monitored patient data and stored patient information. The pacer computes and collects the following monitored pacing data over a programmable period of time: percent pacing, average rate, maximum rate, number of tachycardia episodes and maximum tachycardia duration. The same type of data is also collected on a cumulative basis in registers that can be cleared externally from time to time. In addition, stored information can be selected for telemetry, such as implant data including the number of days since implantation and lead information, patient data and programming data, such as the number of days since the last programming. Physician-generated advisory messages are also stored for telemetering the patient's pertinent medical history and current medication, for example.

In the preferred embodiment, monitored pacer rate maxima and minima are calculated from a running average of a number of beats also used in the automatic overdrive mode. Other features of the disclosed pacer include software runaway protection which turns the pacer OFF when the pacer timer produces a rate higher than the programmed rate by a predetermined percentage.

BRIEF DESCRIPTION OF THE DRAWINGS

FIG. 12 is a block diagram and schematic representation of means for downloading software into RAM after implantation.

FIGS. 13–17 are representations of electrocardiograms to illustrate the operation of the following antitachycardia mechanisms, respectively: programmed burst, burst rate scanning, automatic overdrive, programmed critically timed and critically timed scanning.

FIGS. 18–26 are software structure diagrams illustrating the relationship between software modules described in the microfiche appendix as follows:

FIG. 18 represents the software routine architecture of the overall system;

FIG. 19 represents the initialize routine;

FIG. 20 represents the interrogation routine;

FIG. 21 represents the pacing routine;

FIG. 22 represents the sensing interrupt routine;

FIG. 23 represents the pacer output subroutines;

FIG. 24 represents the interrupt service routines;

FIG. 25 represents the real time subroutine; and

FIG. 26 represents the special condition parameter check subroutine.

DETAILED DESCRIPTION OF THE PREFERRED EMBODIMENT

Figure 1:
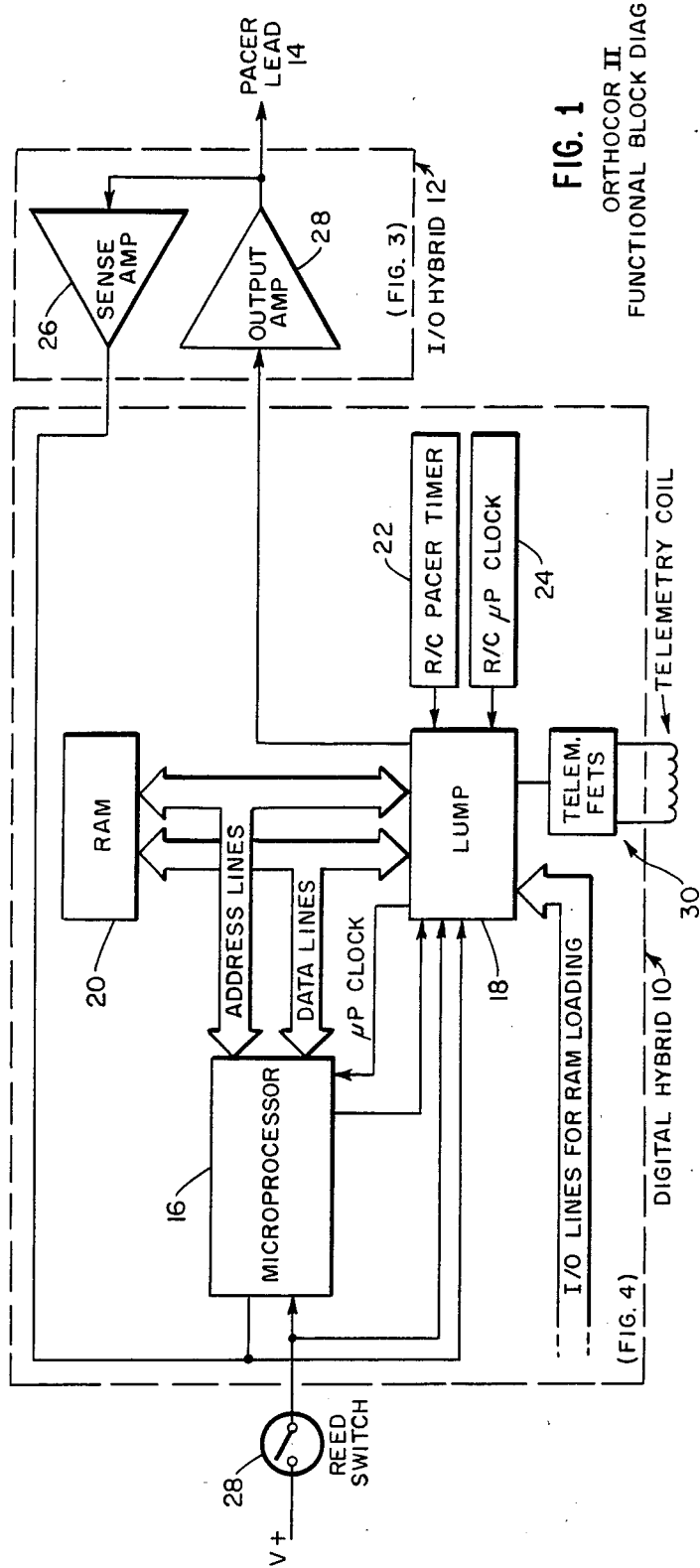
FIG. 1 is a functional block diagram of a cardiac pacer according to the invention.

FIG. 1 illustrates in functional form the overall electronic circuit configuration for an implantable ROMless, single channel, multi-programmable, microprocessor-based cardiac pacer according to the invention. The electronic components of the pacer are sealed together with the lithium compound battery cells (FIG. 5) in a biologically compatible hermetic enclosure, as in the "Orthocor Theta" ™ manufactured by Cordis Corporation, the assignee of the present application. The pacer enclosure itself is implanted at a suitable location in the patient's body and is electrically interconnected with a single standard unipolar or bipolar pervenous pacer lead which terminates in single or dual electrodes, respectively. The lead extends into contact with either the right atrium or the bottom of the right ventricle. The electrically conductive case of the pacer (e.g., titanium) forms the return path or ground electrode in a conventional unipolar electrode arrangement. Since the present pacer is designed for patients with a history of tachycardia, the single channel design was chosen because it allows the bipolar lead necessary for good tachycardia detection, to be used without the dual channel cross talk present in AV sequential pacers.

Linear bipolar leads are required when programming from unipolar to bipolar and are particularly recommended for use because polarity should be programmed to bipolar when the pacer is programmed to an automatic antitachycardia mechanism. Because they have superior sensing and stimulation threshold characteristics, leads with porous-surface electrodes are recommended for use.

TABLE I

| | |
|---|---|
| VVI (Lead in Ventricle) | R-wave inhibited ventricular pacing |
| AAI (Lead in Atrium) | P-wave inhibited atrial pacing |
| VVT (Lead in Ventricle) | R-wave triggered ventricular pacing |
| AAT (Lead in Atrium) | P-wave triggered atrial pacing |
| VOO (Lead in Ventricle) | Asynchronous ventricular pacing |
| AOO (Lead in Atrium) | Asynchronous atrial pacing |

The pacer of the preferred embodiment represents an extension of the Orthocor ™ I pacer (Model No. 234A and 239A), described in the 243,135 application. The Orthocor family of pacers is designed to treat patients with arrhythmia who may require external overdrive of the normal R-wave or P-wave inhibited pacing mode. Like the pacer described in the 243,135 application, the present pacer responds to a magnet applied externally, when programmed to a triggered magnet response mode (AAT or VVT), to operate in synchrony with an overdriver of the type shown in the 243,135 application or with an external pacer to provide the stimulation patterns chosen by the physician for terminating paroxysmal arrhythmias. In addition to this overdrive capability, the disclosed embodiment has five programmable automatic antitachycardia mechanisms which provide the patient with constant tachycardia protection.

The pacer also incorporates a number of new telemetry features, which, along with the antitachycardia mechanisms, are described in detail below.

CIRUIT DESCRIPTION

The electrical component design of the pacer of FIG. 1 is divided into two interconnected hybrids on a folded flex circuit board. A digital hybrid 10 includes the pacing, programming and telemetry logic and I/O hybrid 12 contains the input/output amplifier circuitry connected to the pacer lead 14. The heart of the digital hybrid 10 is a microprocessor 16 operated in conjunction with a semi-custom low power universal array microcomputer peripheral (LUMP) 18 in conjunction with RAM 20. Associated with LUMP circuit 18 are RC networks 22 and 24 for the low power clocks for the microprocessor and pacer timer, respectively.

In contrast to the ROM used, for example, in the 430,507 application, the RAM 20 does not contain any preprogrammed fixed instructions and it must be loaded with the pacer program instructions before the electronics start functioning as a pacer. The LUMP chip contains the input/output transmission gates for loading the RAM. This allows changes to be made in the software without masking new ROMS.

Figure 2:
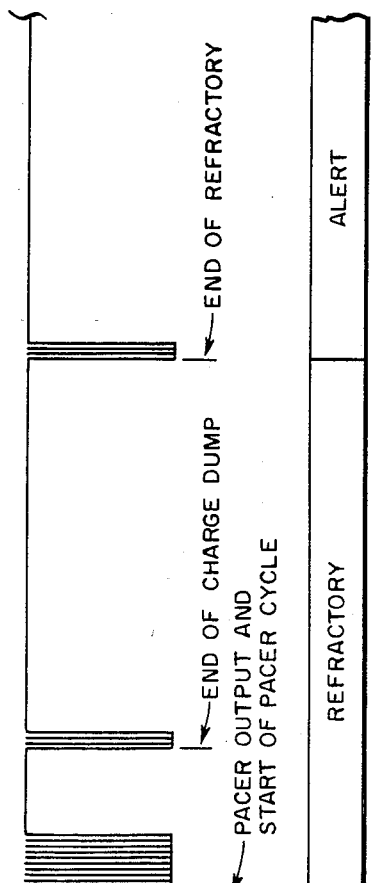
FIG. 2 is a timing diagram of the microprocessor timing cycle.

The LUMP chip 18 acts as a controller or director for all of the operations of the pacer including the running of the microprocessor 16. In a typical cardiac cycle as shown in FIG. 2, the microprocessor 16 is turned ON only at three points. Initially a pacer output command is issued from the microprocessor via the LUMP circuit 18 to an output amplifier 28. At the end of the pacer output, the charge dump cycle begins and the microprocessor clock is halted. The microprocessor is awakened automatically to terminate the charge dump and then turned OFF until the alert period when it comes on to terminate the refractory period by enabling the sense amplifier.

Inputs from sense amplifier 26 are reed 28 are passed to interrupt control circuitry inside the LUMP chip to wake up the microprocessor. At the completion of a given task, the microprocessor turns itself OFF by disabling the microprocessor clock for a "sleep" period duing which the LUMP chip monitors spontaneous cardiac activity, magent, programming or interrogate requests through the reed switch, while timing an interval preset by the microprocessor. Since the microprocessor functional current drain is dependent on the average frequency, it can be reduced by this intermittent mode of operation.

Figure 3:
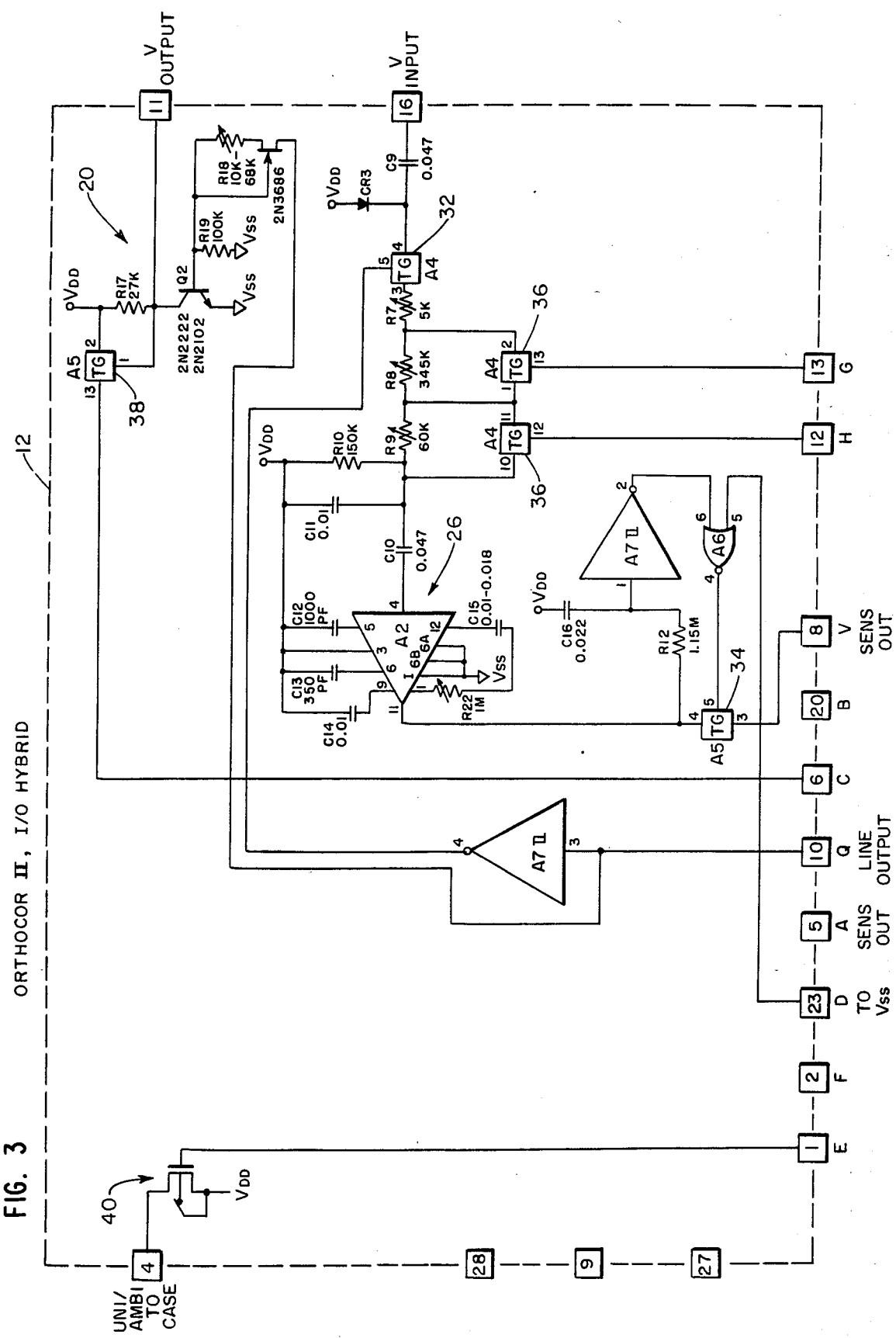
FIG. 3 is an electrical schematic diagram of the I/O hybrid of FIG. 1.

The analog input/output circuitry of the I/O hybrid 12 is shown in detail in FIG. 3. The circuit is essentially the same as that shown in the 207,003 application modified for a single channel operation. However, the rate limit circuit of the corresponding I/O circuit in applications 207,003 and 430,507 is omitted in FIG. 3 of the present embodiment since runaway protection is implemented in software. In addition, the noise inhibit circuit kicks in anywhere above 10 hertz as opposed to 40 hertz in the I/O circuits of the foregoing applications. The sense amplifier 26 is connected between transmission gates 32 and 34 for blanking the sense amplifier, while the sensitivity is adjusted by transmission gates 36. The transmission gates are controlled via output latches on the LUMP circuit 18. The constant current output circuit 28 operates in a similar manner to that of the 207,003 application with transmission gate 38 performing a charge dump on command from the CPU via the LUMP chip.

In addition to the sense and output amplifier circuits, the I/O hybrid of FIG. 3 also has a field effect transistor (FET) 40 for grounding the case of the pacer to the negative supply for unipolar or ambipolar lead configuration. The connections are shown more explicitly in FIG. 5. Control output "E" from the LUMP chip to the I/O hybrid either disconnects the case electrically for true bipolar operation or connects it to ground for unipolar or ambipolar operation. In the unipolar mode, the case is the only ground electrode. In the ambipolar mode, a bipolar lead is used with the remote proximal anode also connected to ground. In true bipolar, the case is disconnected by FET 40.

Figure 4A:
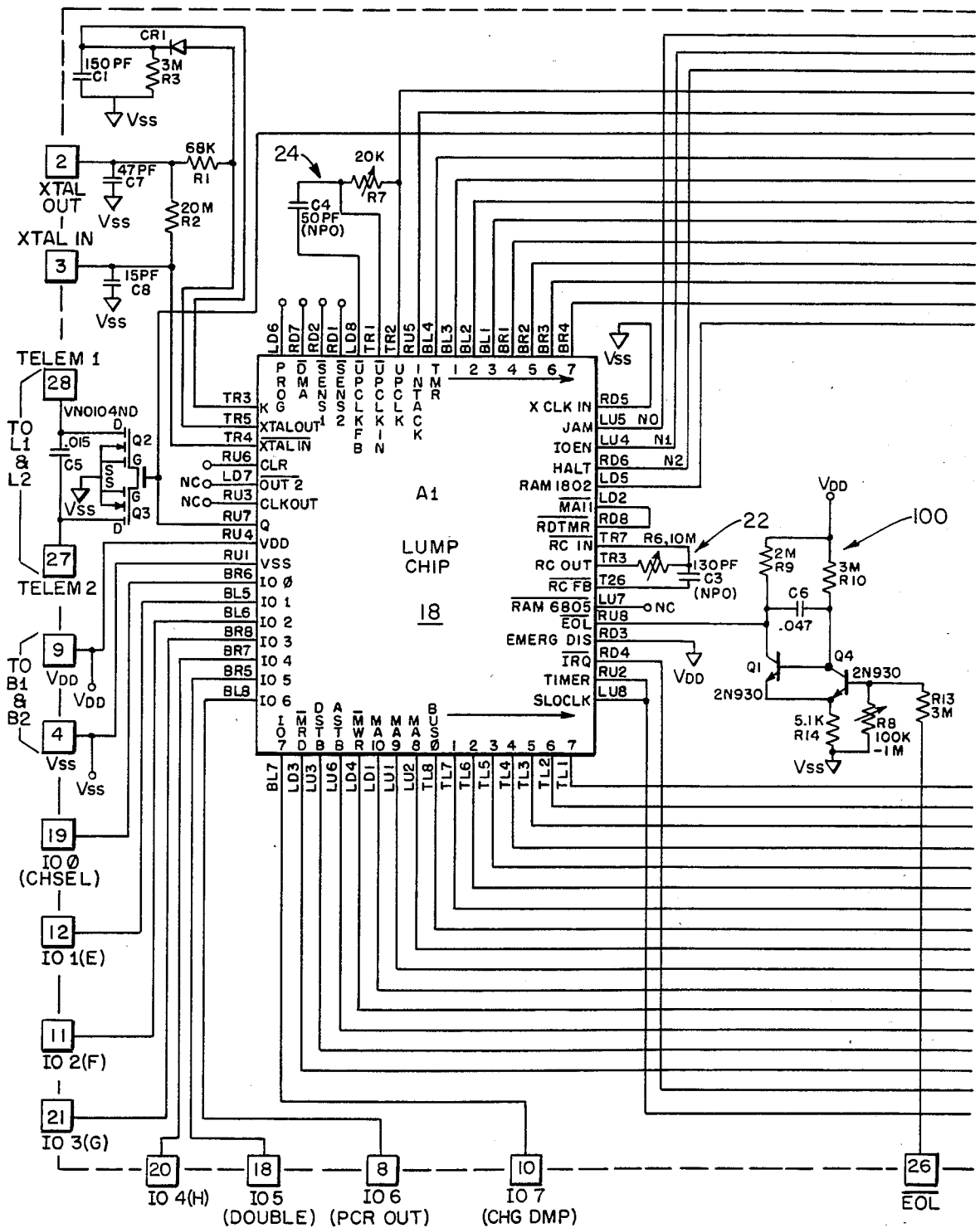
FIG. 4A and 4B are an electrical schematic diagram of the digital hybrid of FIG. 1.
Figure 4B:
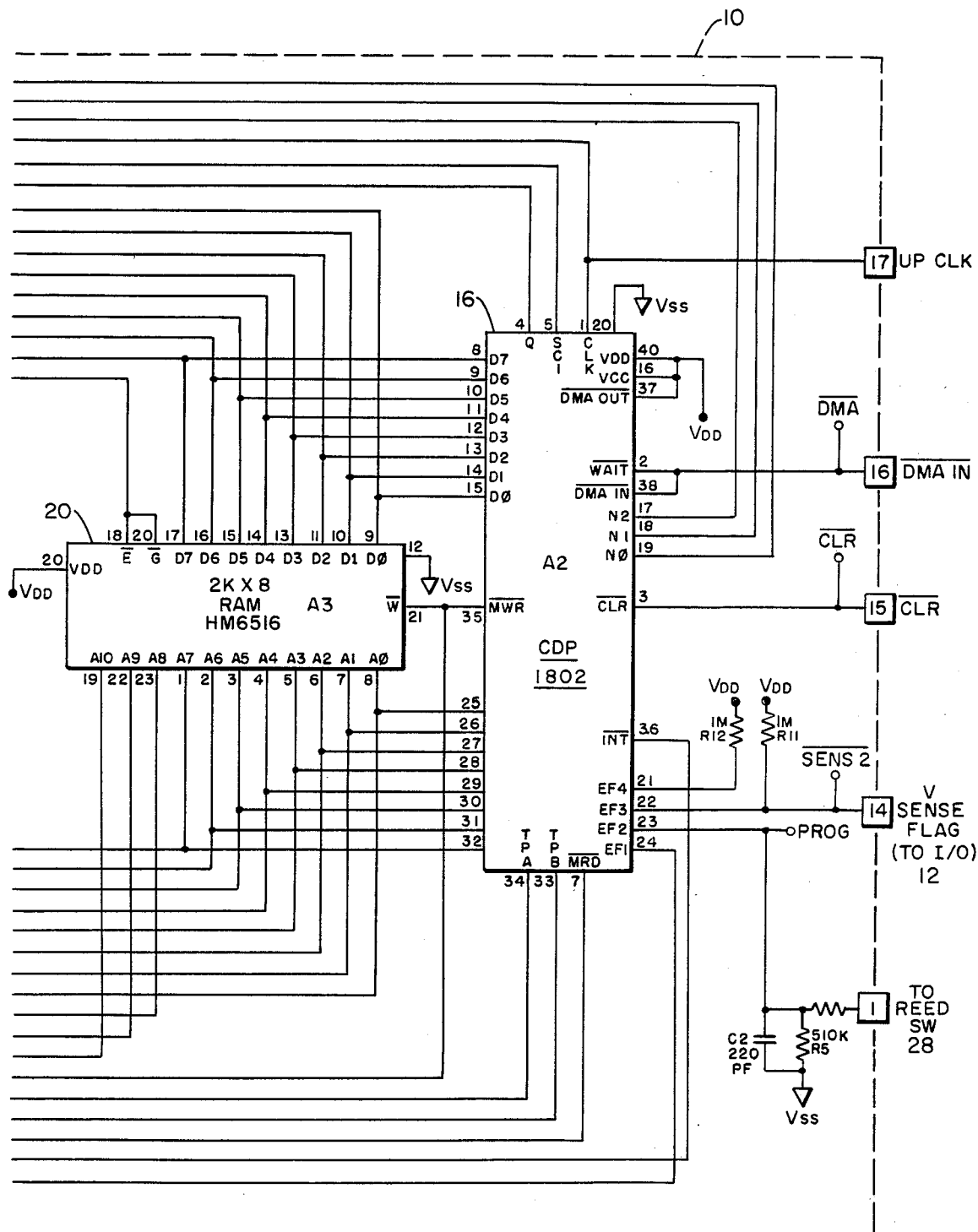
Figure 5:
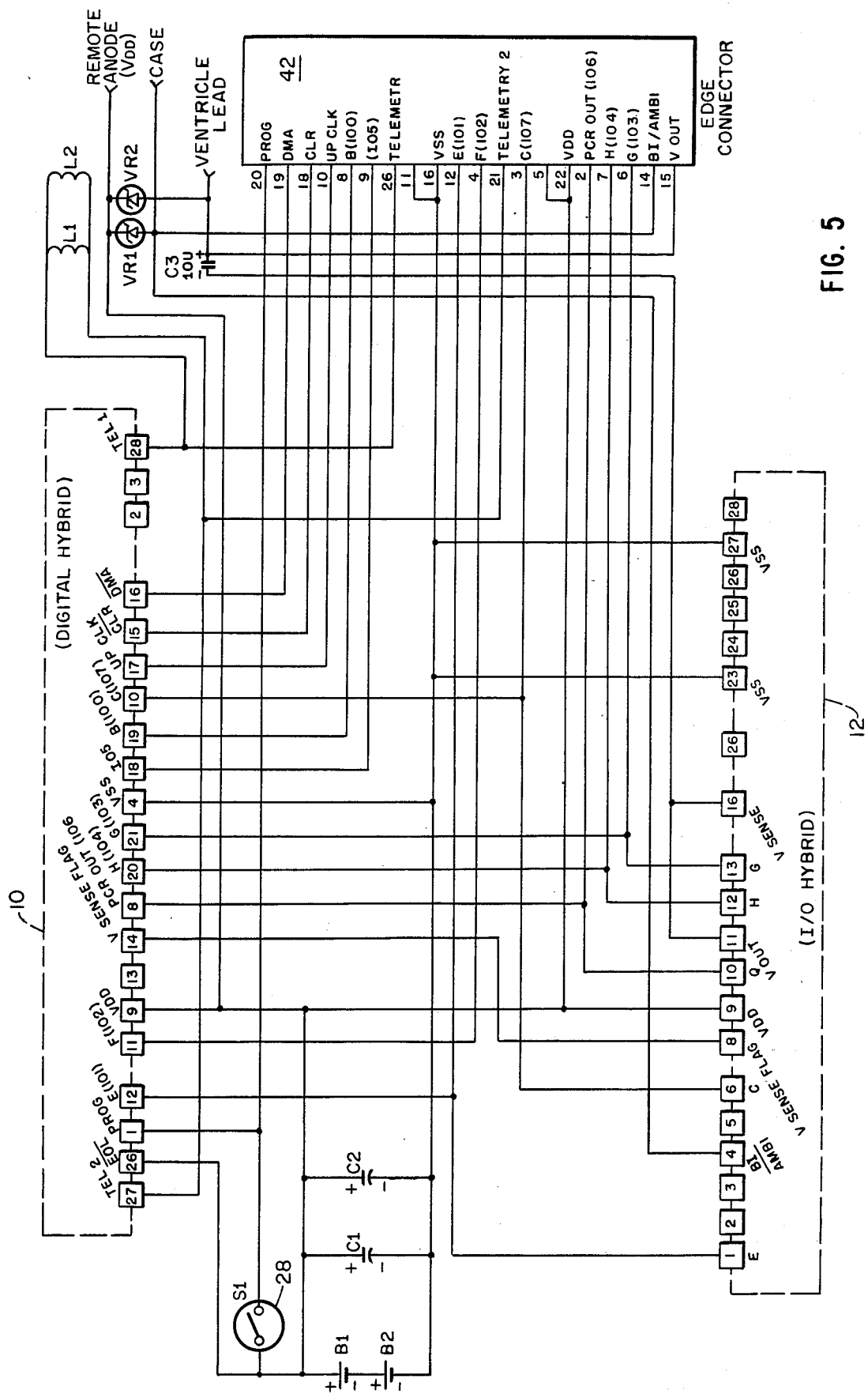
FIG. 5 is an electrical interconnect schematic for the pacer.

FIGS. 4A and 4B shows the interconnections and various accessory components of the three-chip digital hybrid 10. As in FIG. 3, hybrid pins are shown as squares set in the periphery of the hybrid circuit shown in dashed lines. The pin numbers between the digital hybrid 10 and I/O hybrid 12 are interconnected as shown in FIG. 5 with an edge connector 42. The remainder of the components in FIG. 5 external to the hybrid circuits comprise the discrete component which round out the complement of electronic circuitry for the pacer of FIG. 1. In addition to the reed switch 28 (S1), FIG. 5 shows battery cells B1 and B2 along with battery capacitors C1 and C2. Positive battery voltage is $V_{DD}$ is considered the system ground and negative battery voltage $V_{SS}$, nominally minus 4.2 volts, is considered the system supply voltage. Output decoupling capacitor C3 and Zener diodes VR1 and VR2 between the electrodes provide defibrilator shock protection. Flat wound coils L1 and L2 act together as the telemetry coil for output data transmission. Coils L1 and L2 are mounted in parallel on opposite sides between the pacer electronics and the case for equalizing front and rear reception of the carrier.

The digital hybrid 10 of FIGS. 4A and 4B includes standard microprocessor RCA CDP 1802. The 1802 is a CMOS 8-bit bus oriented CPU with sixteen 16-bit internal registers. The chip features direct memory access (DMA) capability. Besides the internal registers, the microprocessor does not happen to have any on-chip memory. The preferred memory is supplied by a 2K×8 (16 kilobits) high speed CMOS low power synchronous static RAM HM6516. This memory contains 2,048 8-bit words containing the program instructions and programmed parameters necessary for the pacer to function. The low power RAM is screened for a maximum of 1 microampere (ua) standby current drain. Like the CMOS microprocessor, the RAM functional current is also frequency dependent. Due to the intermittent operation of the microprocessor clock, the average functional current drain of the RAM is also very low, preferably in the range of 1 to 2 ua.

The third chip of the digital hybrid 10 is the lump chip 18 which is a semi-custom chip based on an RCA standard CMOS gate array. A gate array consists of many uncommitted CMOS logic devices in an integrated circuit (IC). These logic gates are interconnected according to specific requirements. The final metalization of the IC according to the customer requirements, connects the gate array to perform specific functions. A pin description or "pinout" for the LUMP chip 18 is shown in Table II below.

TABLE II

LUMP PINOUT DESCRIPTION

| | |
|---|---|
| $\overline{\text{XTALIN}}$ | crystal input |
| XTALOUT | crystal driver |
| $\overline{\text{RCIN}}$ | backup RC oscillator input |
| RCOUT | backup RC oscillator driver |
| $\overline{\text{RCFB}}$ | backup RC oscillator feedback output |
| $\overline{\text{CLR}}$ | input for starting crystal |
| K | input for frequency discriminator to switch to RC backup if crystal failure occurs. |
| $\overline{\text{EOL}}$ | end of life input to switch from crystal to RC backup when battery depletion occurs. |
| XCLKIN | external clock input may be used in place of the on chip crystal circuit to reduce power consumption if necessary (256 Hz). |
| CLKOUT | 256 Hz clock output is the output frequency of the RC backup, crystal divided by 128 and external clock input. |
| TIMER | 128 Hz output for driving the microprocessor clock timer. |
| EMERGDIS | input for disabling the emergency pacer by hardwiring it to ground. |
| Q | input for driving the pacer output from the microprocessor. |
| SLOWCLK | clock input to the microprocessor clock timer. |
| $\overline{\text{UPCLKIN}}$ | microprocessor clock input. |
| UPCLK | microprocessor clock output driver 160 kHz. |
| HALT | input for stopping the microprocessor clock. |
| PROG | programming input for input logic. |
| $\overline{\text{SENS1}}$ | channel 1 sense amplifier input. |
| $\overline{\text{SENS2}}$ | channel 2 sense amplifier input. |
| $\overline{\text{IRQ}}$ | interrupt request output. |
| $\overline{\text{INTACK}}$ | interrupt acknowledge input for resetting interrupt request. |
| BUS0–BUS7 | input bus for microprocessor clock timer, output ports and high order address latch. |
| TRM0–TRM7 | tri-state output bus from timer or DMA RAM loader. |
| I00–I07 | bi-direction bus for hybrid interface provides input from RAM loader or output drivers for I/O hybrid. |
| $\overline{\text{DMA}}$ | control input for bi-directional I/O bus and TMR bus multiplexors. |
| $\overline{\text{RDTMR}}$ | tri-state control for timer bus. |
| MA8–MA10 | outputs from high order address latch. |
| $\overline{\text{MA11}}$ | inverted output from most significant high order |

TABLE II-continued
LUMP PINOUT DESCRIPTION

| | |
|---|---|
| | address bit. |
| ASTB | address strobe input for latching high order address bits. |
| DSTB | data strobe input for latching high order address bits. |
| $\overline{MRD}$ | memory read input for generating RAM 1802. |
| $\overline{MWR}$ | memory write input for generating RAM 1802. |
| $\overline{RAM}$ $\overline{1802}$ | output for enabling the RAM for an 1802 application. |
| $\overline{RAM}$ $\overline{6805}$ | output for enabling the RAM for a 6805 application. |
| JAM | input for setting the microprocessor clock timer. |
| IOEN | input for changing output port bits. |
| $\overline{BIP}$ | output for driving VMOS FET's for bipolar operation. |
| VSS | negative power input. |
| VDD | positive power input. |

The LUMP chip design strategy allows interfacing with several different microprocessors, namely, the Motorola 6805 or RCA 1804 and 1805, as well as various combinations of RAM, ROM and I/O devices. Although LUMP was intended to be universal in application, several constraints were placed on the design in order to maintain compatability with the existing I/O hybrid (FIG. 3) used in the dual channel configuration for the AV sequential pacer of application Ser. No. 207,003 and 430,507. Because of the universality of the LUMP chip design, however, certain functions of the chip are not used in the present embodiment, namely, crystal oscillator, EOL oscillator substitution, VVI emergency pacer, and all second channel functions.

Figure 6:
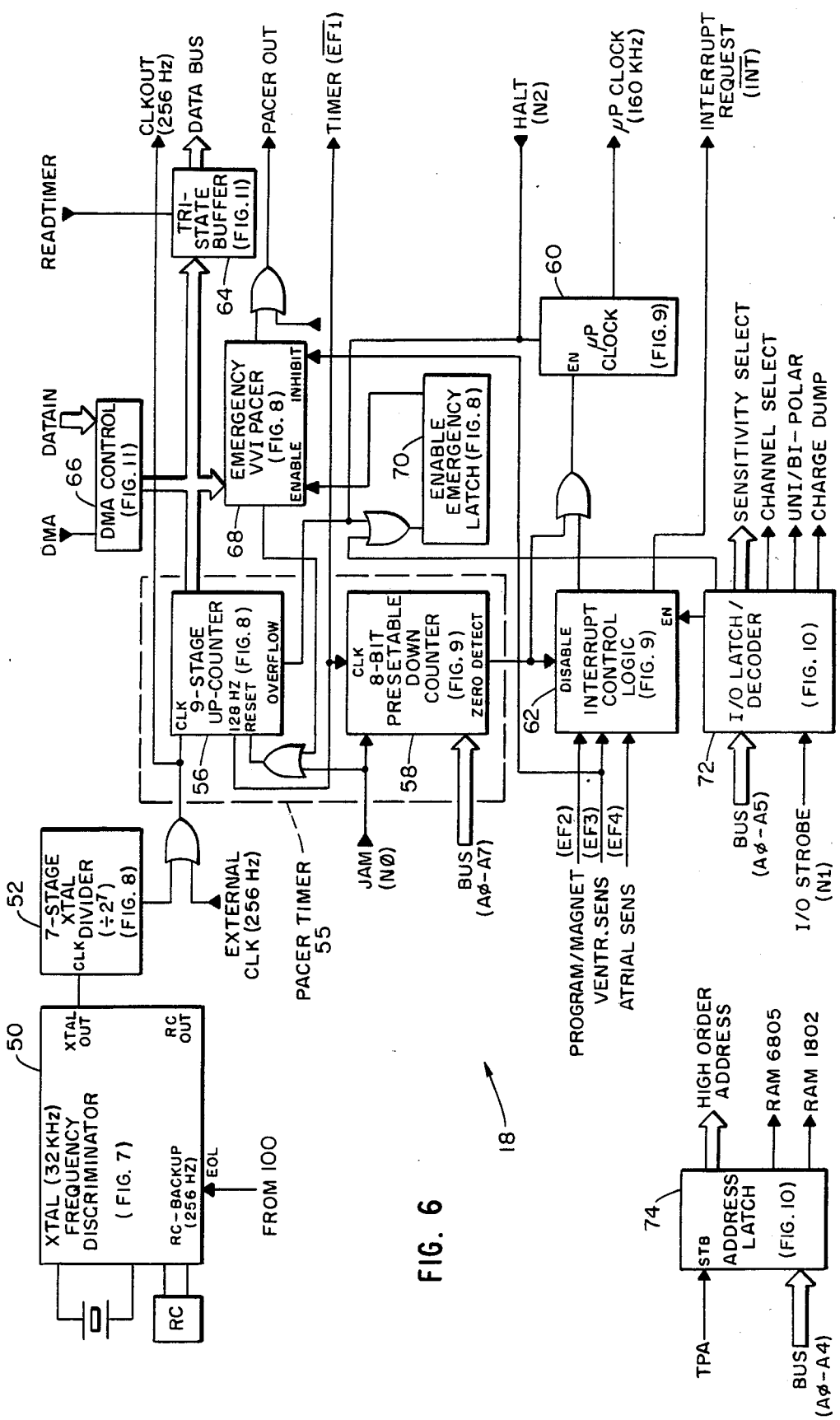
FIG. 6 is a functional block diagram of the LUMP circuit of FIGS. 4A and 4B.

As shown in the LUMP block diagram of FIG. 6, a 32 kilohertz crystal oscillator (not used in this embodiment) is designed to produce a high frequency output which is counted down in divider circuit 52 and passed via OR gate 54 to pacer timer 55 as the 256 hertz clock input to 9 stage up counter 56. Instead, a 256 hertz/RC clock supplies the independent time base for the pacer timer 55. The clock rate is halved to drive an 8-bit presettable down counter 58 which is the heart of the LUMP timing operation. On a JAM signal from the microprocessor, the preset for counter 56 is loaded off of the address bus. The JAM signal also resets the up counter 56 so that the counters 56 and 58 in pacer timer 55 operate in tandem but in different directions. That is, as down counter 58 counts down from the preset, counter 56 counts up from zero. When the down counter 58 times out, its zero detect output enables the microprocessor clock circuit 60 in order to restart the microprocessor 16 and disables the interrupt control logic 62. Simultaneously, the elapsed time can be read from the up counter 56 via tristate buffer 64 onto the data bus associated with the microprocessor 16.

External data can also be read directly into RAM off of the data bus via tristate buffer 64 by means of DMA control logic circuit 66. An emergency VVI pacer 68 (not used in this embodiment) is programmable via the DMA control logic 66 and enabled by emergency latch 70 which in turn is enabled either by the microprocessor via the I/O latch decoder circuitry 72 or by the overflow output of the 9 stage upcounter 56. Counter 56 cannot overflow in normal operation because of presetting of minimum rate and refractory intervals by the microprocessor. The lump chip also contains additional latch circuitry in latch decoder 72 and address latch 74 for selecting sensitivities, channels in a dual channel pacer, unipolar, bipolar or ambipolar mode and charge dump output to the I/O hybrid 12 (FIG. 3). In addition, the address latch 74 latches the high order address to conform to timing requirements of the specific microprocessor. Each of the circuits specified by the functional block diagram in FIG. 6 is developed in more detail in the corresponding FIGS. 7-11.

A rectangle with the pin number inside represents an I/O pad while terminal triangles indicate an internal connection. The I/O pads of FIGS. 7-11 correspond to the pin designations on the LUMP chip 18 of FIGS. 4A and 4B and the LUMP pinout of Table II above.

Figure 7:
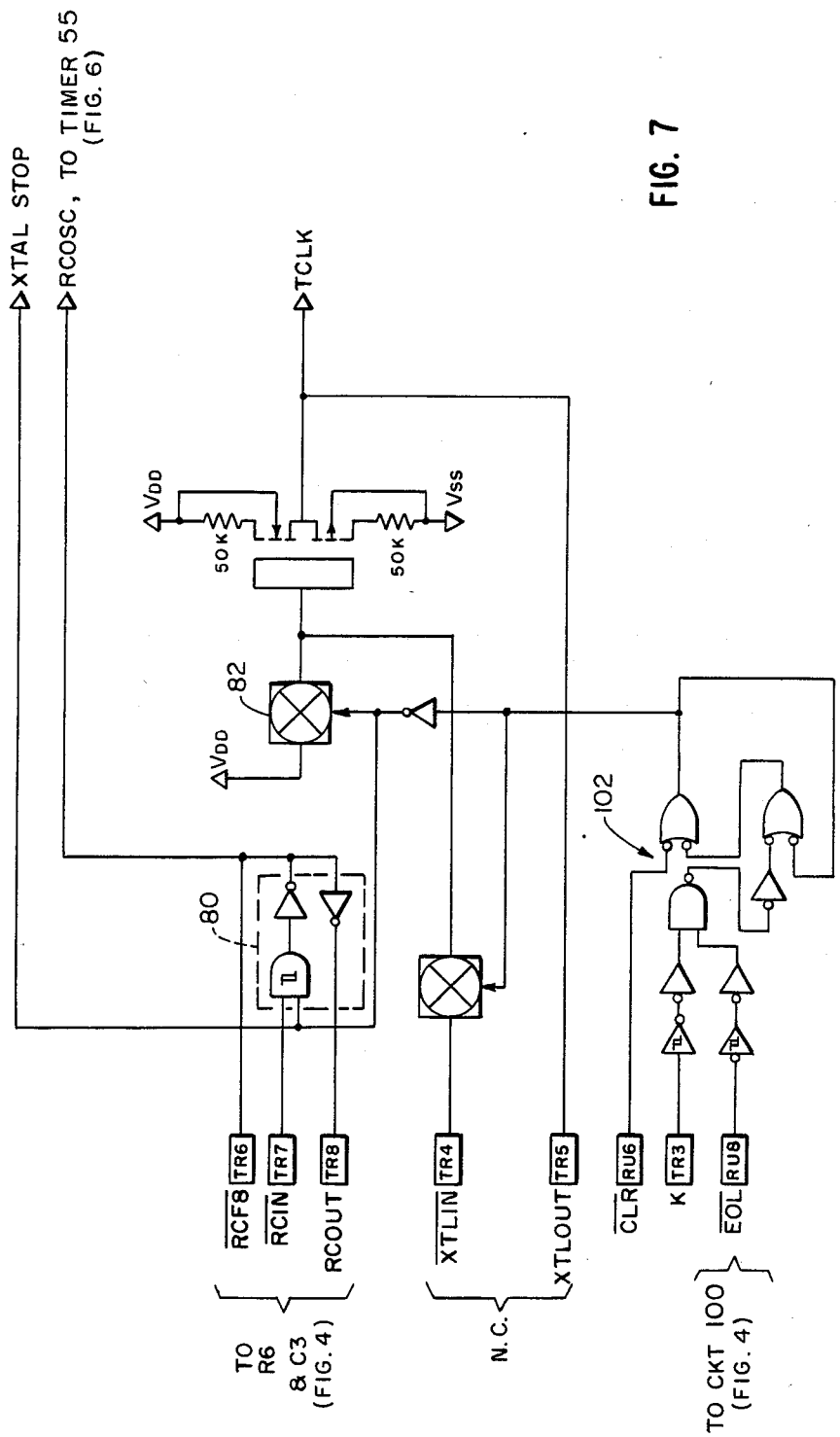
FIG. 7 is a LUMP crystal/RC oscillator backup circuit for the LUMP circuit of FIG. 6.
Figure 8:
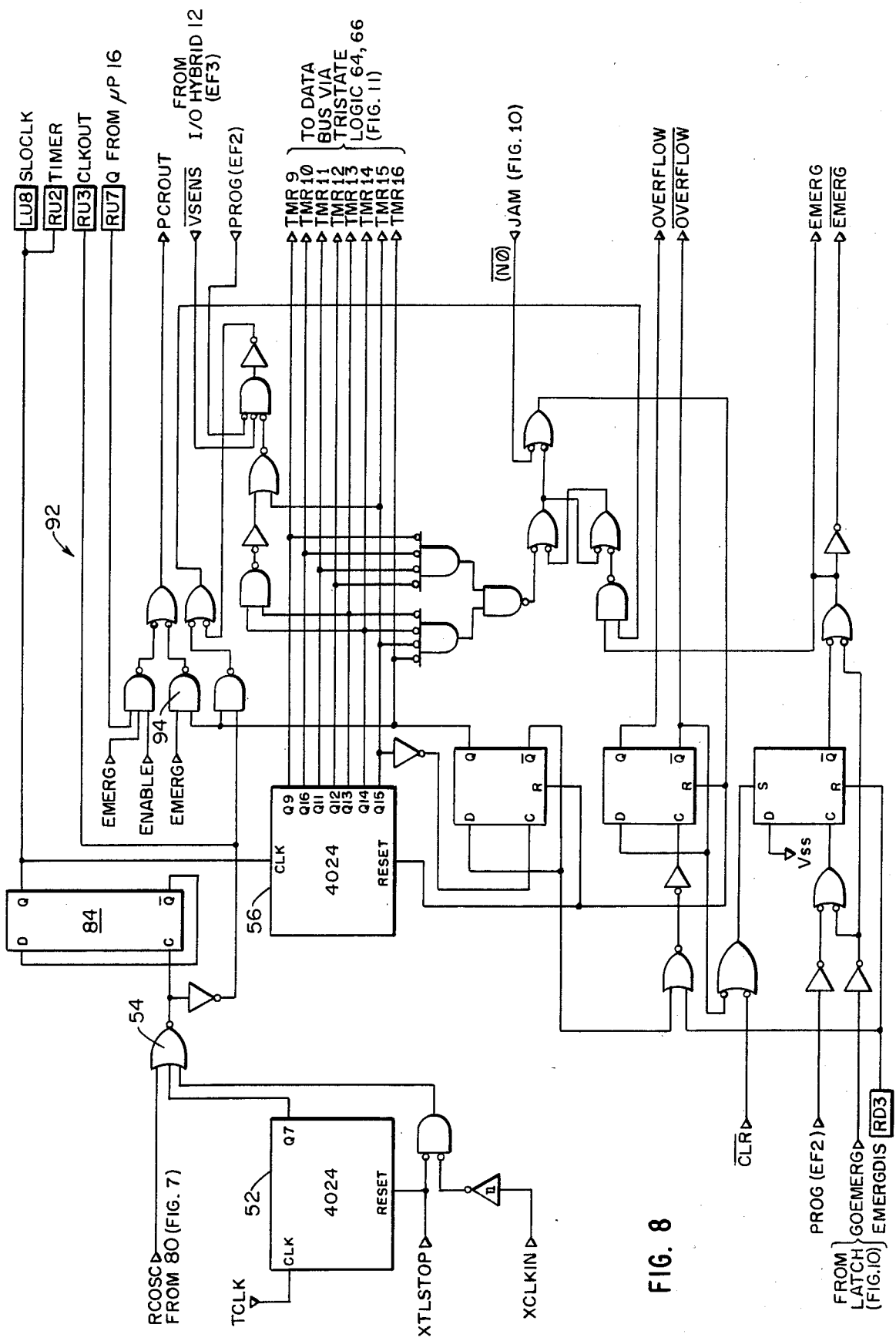
FIG. 8 is a schematic diagram of the pacer timer circuitry and emergency VVI pacer circuitry for the LUMP circuit of FIG. 6.

Discrete accessories for LUMP chip 18 are shown in FIGS. 4A and 4B. For Example, RC OUT and (RC IN)-bar and (RC FB)-bar are connected to the RC circuit of FIGS. 4A and 4B comprising variable resistor R6 and capacitor C3. In conjunction with the Schmitt trigger and inverter components 80 of FIG. 7, the RC network implements an RC oscillator. Similarly, (XTLIN)-bar and (XTAL OUT)-bar are designed to be connected to a crystal via I/O pads 2 and 3 of the overall digital circuit of FIGS. 4A and 4B by way of discrete components in RC circuit comprising resistors R1 and R2 and capacitors C7 and C8. The K input is connected to a frequency discriminator comprising diodes CR1 and RC network C1 and R3. However, in the present embodiment, as shown in FIG. 5, there is no crystal to connect to the hybrid pads 2 and 3. Thus, the crystal oscillator function is disabled via the K signal and gate 82 so that the only operational output from the circuit of FIG. 7 is RC OSC. With the TCLK input from FIG. 7 omitted, the divide by 7 circuit 52 of FIGS. 6 and 8 is, of course, unused, the only output from gate 54 being due to the RC oscillator. This rate is divided in half by flip flop 84 of FIG. 8 and passed via the I/O pad designated TIMER as the clock input ("SLO CLK" LUMP pin LU8) to the presettable down counter 58. In addition, the Q output of flip flop 84 forms the clock input to 9 stage up counter 56 of FIG. 8. The higher order byte count (Q9-Q15) of the up counter 56 is placed on the data bus for use by the microprocessor 16 via the tristate buffer logic 64 of FIG. 11.

Figure 11:
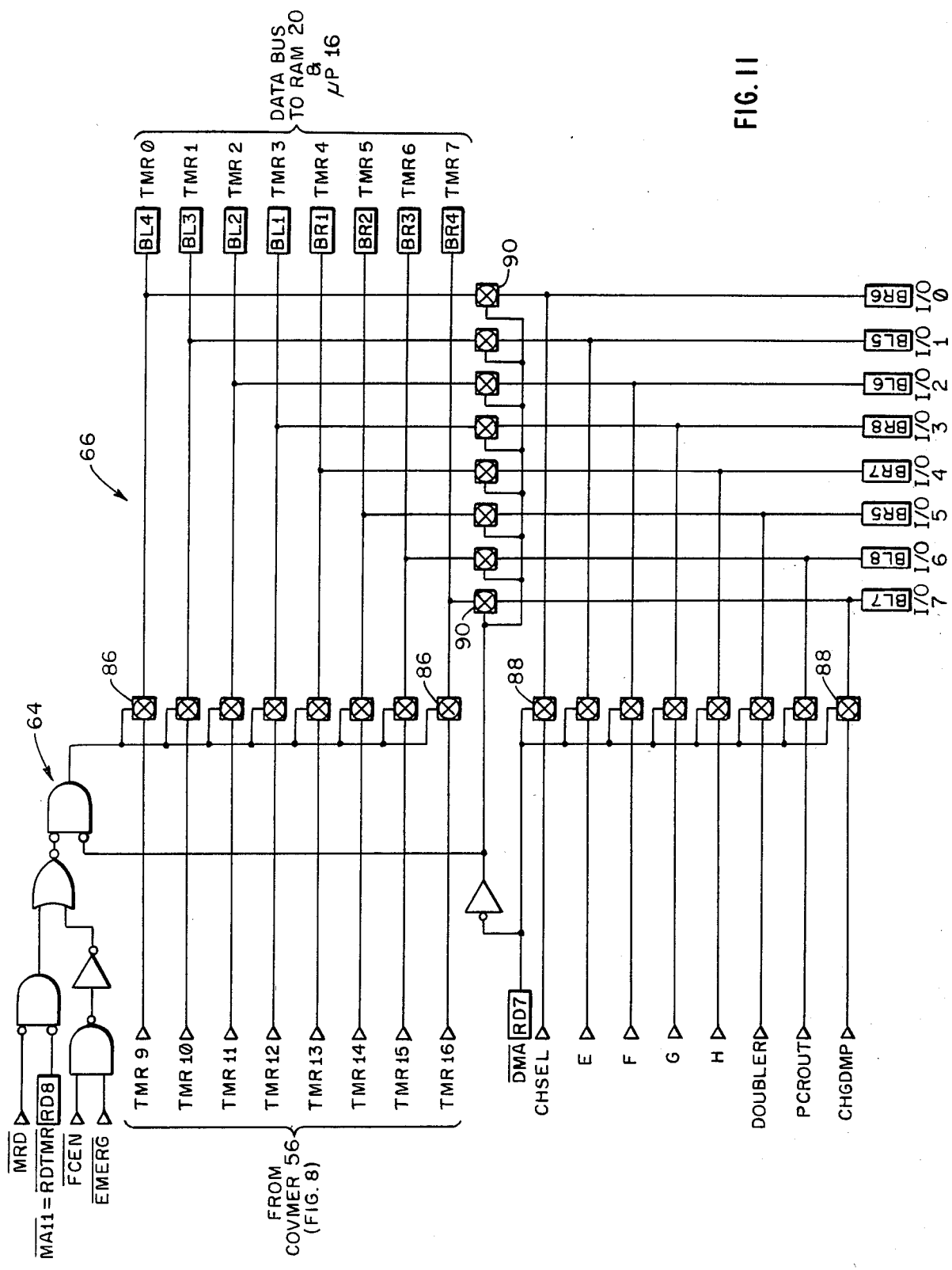
FIG. 11 is a schematic diagram of the DMA control logic for the LUMP circuit of FIG. 6.
Figure 22:
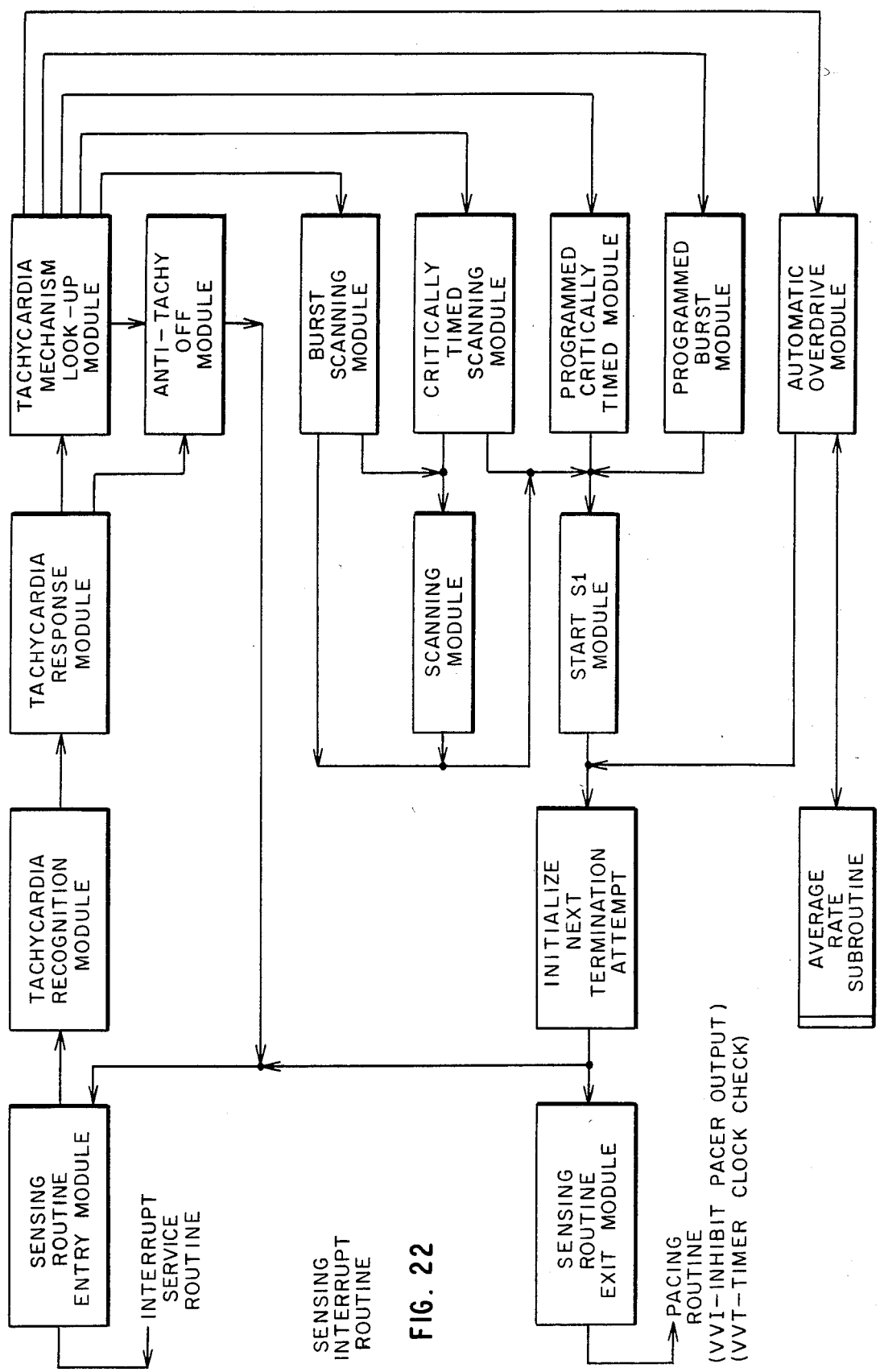
Figure 23:
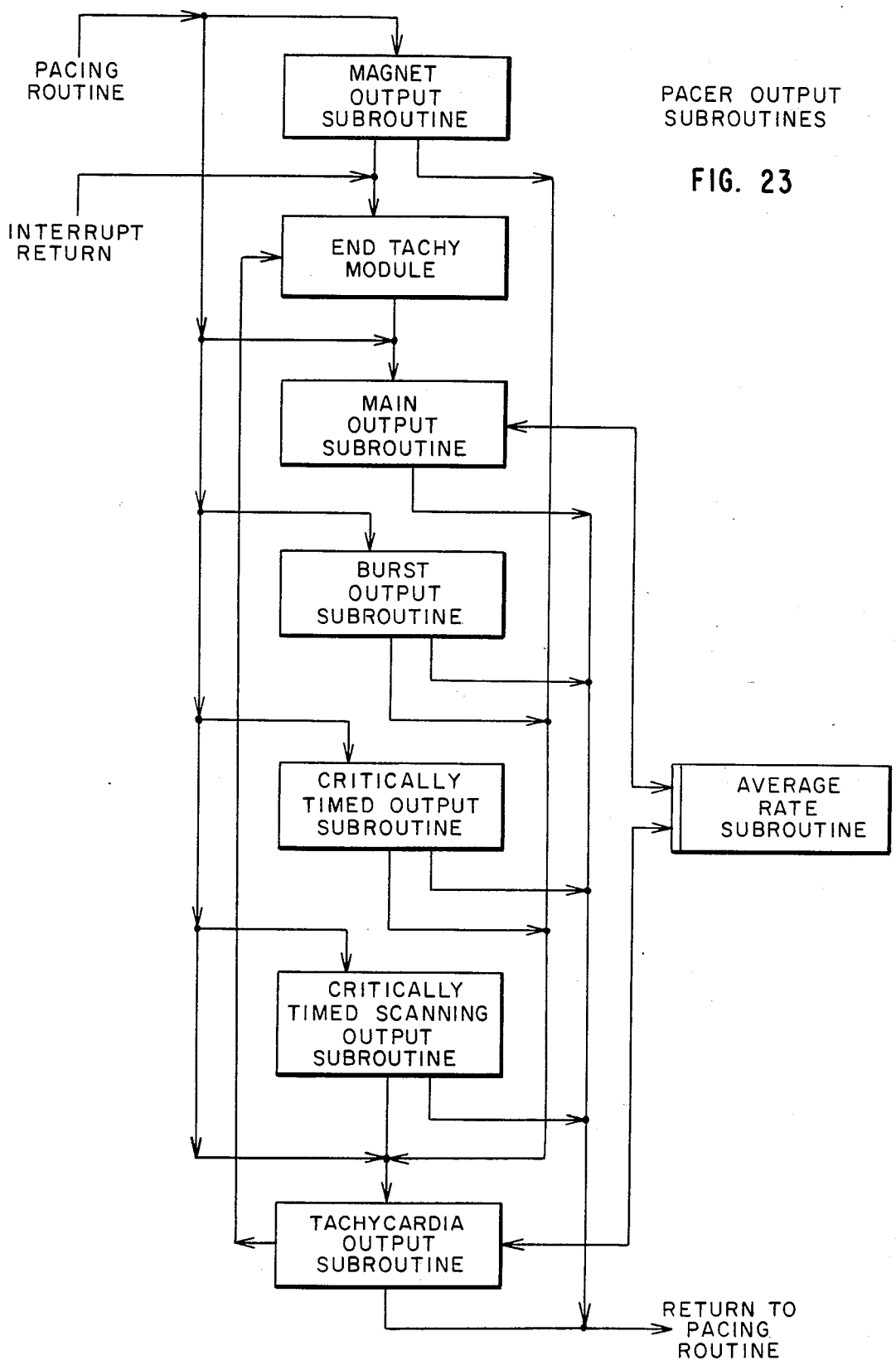
Figure 24:
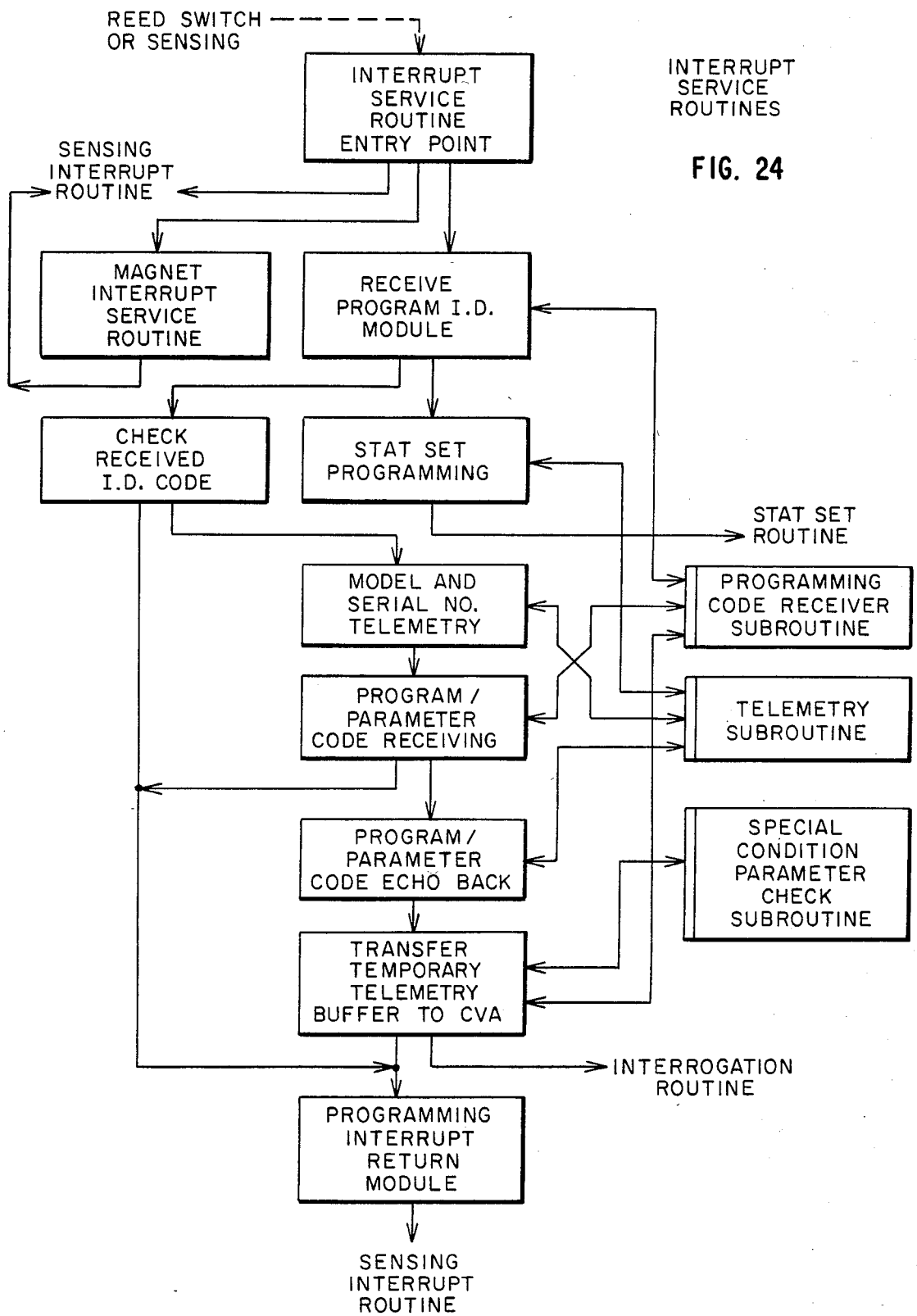

By means of the DMA control logic 66 of FIG. 11, the parellel output from counter 56 is passed via parallel gates to the data bus or timer bus directly to RAM 20 and microprocessor 16. The I/O lines, "channel select" (CHSEL), E, F, G, H, DOUBLER, PCROUT, CHGDMP, are normally connected to the I/O LUMP pins 0-7. However, for factory loading software into RAM 20, the DMA signal disables the timer gates 86 and internal I/O gates 88 and enables the I/O gates 90 which connect the LUMP I/O pins to the data bus via the timer lines. This enables the RAM to be loaded directly over the I/O lines.

The RCA 1802 microprocessor provides two I/O lines for byte transfer between memory and I/O devices. These lines are called direct memory access (DMA) lines. Activating the DMA in-line causes an input byte to be immediately stored in a memory location in RAM without intervention by the program being executed. The DMA-out line causes a byte to be immediately transferred from memory to the requesting output circuits. The DMA-out function is not employed in the LUMP circuit. A built-in memory pointer register is used to indicate the memory location for the DMA cycles. Resetting the 1802 initially sets this pointer to a beginning memory location. Each DMA byte transfer automatically increments the pointer to the next higher memory location. Repeated activation of the DMA in-line causes transfer of any number of consecutive bytes via the I/O lines into the RAM, independent of concurrrent program execution.

DMA RAM loading can be accomplished by the pacer manufacturer to load operating software into RAM. The RAM can also be loaded by inbound telemetry via the external programmer. (See FIG. 12.) In that system, software is transmitted in serial bit fashion, rather than byte by byte. The instruction data is received in registers and transferred byte by byte into the RAM via the normal memory addressing system, rather than the DMA system, for consecutively addressing each instruction byte to a respective RAM location. For example, an operating system stored beginning at RAM location 0770 could be accessed via a programming command to load transmitted instruction bytes into consecutive addresses beginning at RAM address 0000 to write over the existing software. A command following the last downloaded instruction byte would cause reinitialization of the microprocessor (via the special operating system) to the beginning point of the down loaded program by resetting the program counter register in the microprocessor.

Additional control logic in circuit 64 of FIG. 11 governs the timing of the byte transfer from the downcounter 56 out onto the data bus in accordance with the state of the memory READ signal (MRD) and READ TIMER (RDTMR). The memory read level gates the timer byte onto the data bus for use by the microprocessor forms the tristate control for the timer bus. The read timer input is provided directly from the microprocessor as the inverted most significant high order address bit (MA11).

The stimulation output of the pacer is timed by the Q output of the microprocessor which is presented to the Q LUMP input pin and passed to logic circuitry 92 of FIG. 8. Unless the pacer is in the emergency mode or the output is disabled by software (enable signal latched via address bus latch 72, FIG. 10), the Q output (PCROUT) is presented to the I/O hybrid Q input (pad 10 of the I/O hybrid). In the emergency mode (not used in this embodiment), the pacer output can also be formed by gate 94. The remainder of the logic circuitry associated with the output of counter 56 is used for reset logic control. The counter 56 is reset by sensed electrical activity (VSENS) or by attaining a predetermined count in the unused emergency mode, by programming, or by a JAM input which also presets the down counter 58. In the emergency mode a predetermined count is reset by sensed electrical activity to implement a discrete digital pacing logic function to realize the VVI or AAI pacing mode. As this pacing logic is driven directly by counter 56 independently of the microprocessor, the emergency pacer when enabled is not affected by the microprocessor or the microprocessor clock. In the present embodiment the emergency mode is disabled by grounding EMERGDIS (LUMP pin RD3), as shown in FIGS. 4A and 4B. It is enabled by tying EMERDIS to $V_{SS}$, if desired.

Figure 9:
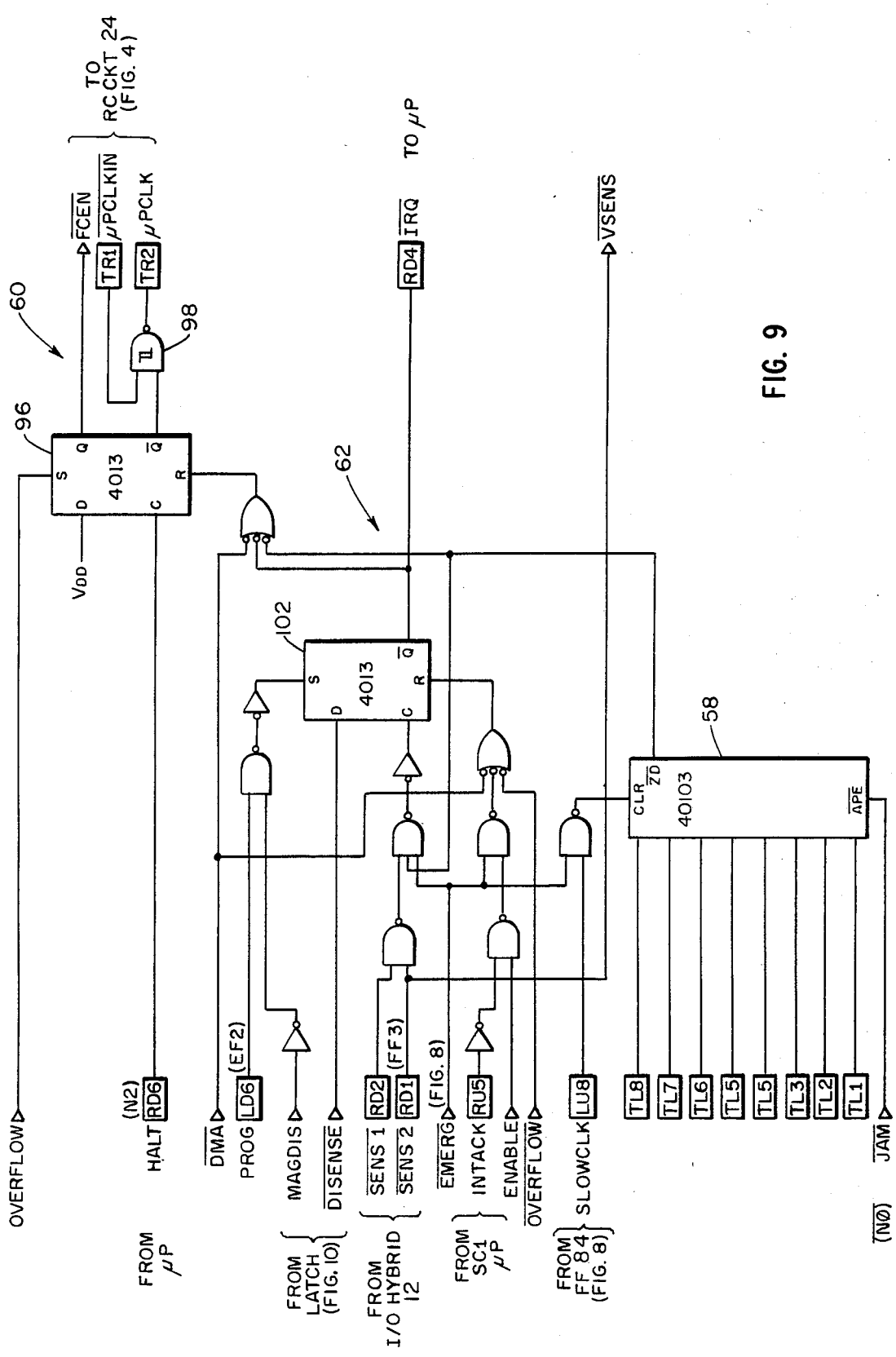
FIG. 9 is a schematic diagram of the processor clock and interrupt logic circuitry for the LUMP circuit of FIG. 6.
Figure 10:
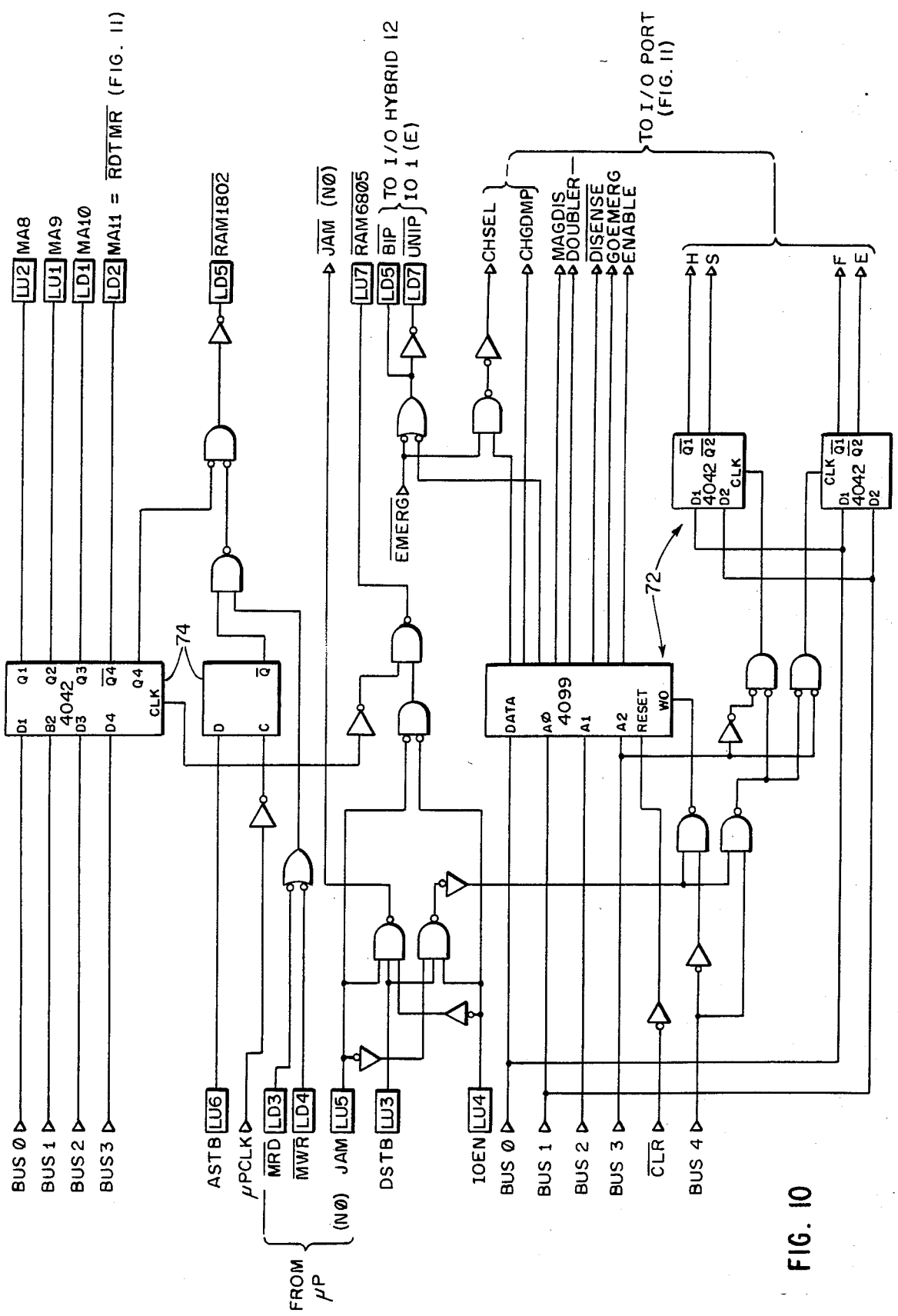
FIG. 10 is a schematic diagram of the I/O RAM interface logic for the LUMP circuit of FIG. 6.

The LUMP microprocessor clock 60 and interrupt logic 62 are shown in FIG. 9. The microprocessor clock control circuit is based on flip flop 96 whose Q-bar output is connected via Schmitt trigger 98 to LUMP pins TR1 and TR2. As shown in FIGS. 4A and 4B, these pins are connected to an external discrete RC circuit comprising C4 and R7. The RC circuit with Schmitt trigger 98 forms a fast low power RC oscillator whose output is taken from pin TR2 and applied to the clock input of the microprocessor. When the Q-bar output of flip flop is high, the microprocessor clock (oscillator) is enabled. The state of flip flop 96 is controlled by both software and hardware. The Q-bar output of flip flop 96 goes high and starts the microprocessor clock whenever the flip flop 96 is reset. During normal operation in the VVI mode, the clock is restarted via the reset line by the down counter 58 timing out (ZD), by reed switch closure or by sensed electrical activity. The microprocessor is stopped via the clock input to the flip flop 96, when the microprocessor sends a halt command over the N2 I/O line. In addition, an overflow condition of the 9-stage upcounter 56 also disables the microprocessor clock. Once disabled, the microprocessor clock is not restarted until the down counter 58 times out or a reed switch or sensed cardiac event occurs.

The LUMP chip 18 is equipped with an automatic end of life (EOL) indicator system. As shown in FIG. 5, the EOL pad number 26 on the digital hybrid 10 is connected to the $V_{DD}$ side of the battery. On the digital hybrid itself in FIGS. 4A and 4B, and the EOL pad 26 is connected via a voltage level comparater circuit 100 to the LUMP pin RU8 (EOL). Inside the LUMP chip 18, as shown in FIG. 7, the EOL signal indicative of the low battery condition is passed to logic circuit 102. If the LUMP timer crystal is in use, the EOL signal, coming toward the end of the battery life of the pacer, substitutes the RC oscillator associated with RC circuit R6 and C3 of FIGS. 4A and 4B. This has the effect of decreasing the asynchronous rate to a noticeable degree to alert the patient or physician to the battery condition.

The VSENS flag input pad 14 on the digital hybrid of FIGS. 4A and 4B is connected to the VSENS output pad (pad 8) from the sense amplifier 26 on the I/O hybrid of FIG. 3. When the sense amplifier circuitry qualifies an electrical signal on the ventricular lead, the VSENS flag (inverted) is applied to the SENS2 input pad on LUMP chip 18. The appearance of the inverted SENS2 signal clocks flip flop 102 of FIG. 9 to reset flip flop 96 to start the microprocessor clock. If sensing is disabled as in the asynchronous mode, the appearance of the sense signal will have no effect since the data input to flip flop 102 will be tied to the other voltage level. In addition to restarting the microprocessor clock, the output of flip flop 102 presents an interrupt request to microprocessor 16. The microprocessor jumps from the main pacing routine to an interrupt service routine. By checking whether (and how long) a reed switch input is present at EF2, the microprocessor determines whether the interrupt requst was due to programming, magnet or VSENS, i.e., sensed cardiac activity, and then executes the appropriate interrupt routine, namely programming interrupt, magnet interrupt or the sensing routine.

The reed switch is connected to microprocessor terminal EF2 and the PROG LUMP pin (LD6, FIGS. 4A and 4B). Inside the LUMP chip 18, as shown in FIG. 6, a reed switch actuation by programmer or magnet is handled by the interrupt control logic 62 which enables the microprocessor clock 60 while sending an interrupt request to the microprocessor.

The Q output of microprocessor 16 is connected to the telemetry coils via field effect transistor (FET) drivers Q2 and Q3 of FIG. 4 which shunt capacitor C5. Digital telemetry of data is effected using pulse width modulation in which FET's Q2 and Q3 are either on or off to transmit serial data in the interrogate mode. The telemetry transponder is described in more detail in U.S. Pat. No. 4,361,153 incorporated by reference. In addition, the Q output of the microprocessor 16 times each output stimulation pulse. The Q output is connected to the Q input (pad RU7) of LUMP chip 18 which forms the pacer output pulse via logic circuitry 92 of FIG. 8. Notice, however, that the same Q input is always connected to the FET's Q2 and Q3. Thus, the telemetry coils are modulated by the stimulation pulse width in real time. This enables an external programmer module with a telemetry receiver to "listen in" on the stimulation pulses as they are being applied to provide a direct indication of pacer rate and pulse width.

FUNCTIONAL DESCRIPTION

The fundamental pacing modes (i.e., asynchronous, inhibited and triggered) are indicated in Table I, supra. The programmable parameters are listed below in Table III.

TABLE III

PROGRAMMABLE PARAMETERS

| | | |
|---|---|---|
| 1. | Minimum Rate | 30–150 PPM in 5 PPM increments and OFF |
| 2. | Hysteresis | 0, 75, 100, 125, 150, 175, 200, 250, 300 msec. |
| 3. | Pulsewidth (Amplitude fixed at 5.5 ma) | .2, .3, .4, .5, .6, .7, .8, .9, 1.0, 1.5, 2.0 msec. |
| 4. | Polarity | Bipolar, ambipolar (with bipolar lead) Unipolar (with unipolar lead) |
| 5. | Refractory | 150, 175, 200, 250, 300, 350, 400 500 msec. |
| 6. | Sensitivity | .8, 1.5, 2.5 |
| 7. | Pacing Mode | VOO, VVI, VVT (with Ventricular lead) AOO, AAI, AAT (with Atrial lead) |
| 8. | MAGNET RESPONSE | |
| | RATE: | 30–150 PPM in 5 PPM increments |
| | Mode: | AAT, AOO, VVT, VOO |
| | Polarity: | Ambipolar with bipolar lead, Unipolar with unipolar lead |
| | Refractory: | 150, 175, 200, 250, 300, 350, 400, 500 msec. |
| | Auto. Anti-tachycardia Mechanism | OFF |
| 9. | Tachycardia Detection | |
| | A. Tachycardia Recognition Rate | 100–180 PPM in 5 PPM increments 200, 220 PPM |
| | B. Tachycardia Recognition Count | 4–25 in steps of 1 |
| 10. | Automatic Anti-tachycardia Mechanisms | |
| | A. Programmed Burst | |
| | *1. Atrial Burst Rate | 120–300 PPM in 10 PPM increments 400–1000 PPM in 100 PPM increments |
| | Vent. Burst Rate | 120–300 PPM in 10 PPM increments |
| | 2. No. of Pulses in Burst | 1–30 |
| | 3. Ramp Steps | 0, ±8, ±15, ±23, ±31 msec. |
| | B. Burst Rate Scanning | |

TABLE III-continued

PROGRAMMABLE PARAMETERS

| | | |
|---|---|---|
| | *1. Atrial Min. Burst Rate | 120–300 PPM in 10 PPM increments 400–1000 PPM in 100 PPM increments |
| | Vent. Min. Burst Rate | 120–300 PPM in 10 PPM increments |
| | *2. Atrial Max. Burst Rate | 120–300 PPM in 10 PPM increments 400–1000 PPM in 100 PPM increments |
| | Vent. Max. Burst Rate | 120–300 PPM in 10 PPM increments |
| | *3. Atrial Present Burst Rate | 120–300 PPM in 10 PPM increments 400–1000 PPM in 100 PPM increments |
| | Vent. Present Burst Rate | 120–300 PPM in 10 PPM increments |
| | 4. Scan Delta | 0, −8, −15, −23, −31 msec. |
| | 5. No. of Pulses in Burst | 1–30 |
| | 6. Ramp Steps | 0, ±8, ±15, ±23, ±31 msec. |
| C. | Automatic Overdrive | |
| | 1. Overdrive Constant | 20–100 msec. in 20 msec. increments |
| | 2. Number of Pules | 1–30 |
| | 3. Ramp Steps | 0, ±8, ±13, ±23, ±31 msec. |
| | *4. Atrial Max. Overdrive Rate | 120–300 PPM in 10 PPM increments 400–1000 PPM in 100 PPM increments |
| | Vent. Max. Overdrive Rate | 120–300 PPM in 10 PPM increments |
| D. | Programmed Critically Timed | |
| | 1. S1 (First Critically Timed Interval) | 160–500 msec. in 20 msec. increments. |
| | 2. S2 (Second Critically Timed Interval) | 0, 160–500 msec. in 20 msec. increments. |
| | 3. S3 (Third Critically Timed Interval) | 0, 160–500 msec. in 20 msec. increments. |
| E. | Critically Timed Scanning | |
| | 1. Minimum Premature Interval | 160–500 msec. in 20 msec. increments |
| | 2. Maximum Premature Interval | 160–500 msec. in 20 msec. increments |
| | 3. S1 (present value) | 160–500 msec. in 20 msec. increments |
| | 4. S2 (present value) | 0, 160–500 msec. in 20 msec. increments |
| | 5. Scan Delta | 0, −8, −15, −23, −31 msec. |
| F. | OFF | |
| G. | Termination Attempts (maximum number) | 1, 2, 3, 4, 5, 10, 15, 20, 30, 40, 50 or infinity |
| 11. | Short-Term Monitored Pacing Data | |
| | A. Duration | 0.2, 0.4, 1, 2, 4, 6, 12, 24 and 48 hours |
| | B. Block Size | 1/12 of duration, e.g. 2 hr. blocks over 24 hrs. |
| 12. | Stat Set | VVI/AAI, 70 PPM 1.0 msec. PW, 1.5 MV sensitivity, 300 msec. refractory, unipolar/ambipolar, Auto. Anti-tachycardia Mechanism OFF, Hysteresis 0 |
| | Non-Programmable Parameters | |
| | Output Voltage, Volts (Open Circuit) | 4.0 |
| | Output Current, mA | 5.5 |
| | E.O.L. Indicator | 5% or more rate decrease |
| | Rate Increase Protection | Pacer turns off if min. rate increases to 14% more than its programmed value. |

*The 400–1000 PPM will be locked out by the Programmer when user selects Vent. lead location.

In addition to the usual programmable parameters of minimum rate, pulsewidth, refractory period, cardiac sensitivity and pacing mode, a number of new programmable parameters are introduced. The hysteresis interval and magnet response mode is made variable along with the tachycardia threshhold rate, recognition count, short-term monitor and five individually programmable antitachycardia mechanisms. Stat set (paragraph 12 of Table III) is a default mode which is introduced in the initialization routine or armed by the stat set button on the programmer. In stat set, the pacer operates as a VVI or AAI pacer depending on the lead location at 70 pulses per minute with nominal pulse width, sensitivity and refractory periods and the case connected as an anode. In addition, the antitachycardia mechanisms are off as is the hysteresis function.

The non-programmable end of life (EOL) indicator in the present embodiment is a natural function of the decaying battery voltage. That is, the pacer timer 55 is operated exclusively by an RC oscillator which is voltage dependent. Because the crystal clock is not used for the pacer timer, the end of life circuit 100 does not switch the pacer timer clock from the crystal to the RC oscillator. Instead, the frequency of the RC oscillator declines as a function of the battery voltage. The asynchronous pacer rate is directly proportional to the RC clock frequency and adequately indicates a substantial decrease in battery voltage.

Once the pacer software is loaded, the microprocessor monitors and controls all of the events within the pacer, according to the programmed parameters. In the VVI mode, for example, as shown in FIG. 2, the pacer issues an output command via the microprocessor Q output to start the pacer cycle and begins charge dump by latching gate 38 of FIG. 3 via I/O 7. At this point, the microprocessor calculates the remainder of the charge dump interval and enters the charge dump interval into the presettable down counter 58 (FIG. 6) via the address bus on command of the JAM output from the microprocessor command lines (N). Simultaneously, the up counter 56 is reset to zero, following which the microprocessor clock 60 is stopped by the HALT command (N2) from the microprocessor 16. While the microprocessor is asleep, the 256 hertz RC oscillator clocks the pacer timer 55. When the down counter 58 times out, like an alarm clock, the zero detect output renables the microprocessor clock 60 to run the microprocessor briefly to unlatch the charge dump line I/O 7, thus ending the charge dump. The zero detect output also disables the interrupt capability until the microprocessor resets the pacer timer 55 after completing its prescribed task. Next, the microprocessor puts itself to sleep by issuing a HALT instruction to the microprocessor clock 60 after loading a number via the address bus into the down counter 58 corresponding to the remainder of the refractory period, during which of course the pacer stimulation logic is non-responsive to cardiac activity. When the down counter 58 times out, the refractory period is over and the microprocessor is restarted to re-enabling the sense amplifier function by inverting an internal register indicator flag in the microprocessor. Next, the microprocessor calculates the remainder of the minimum rate interval and loads a corresponding number via the address bus into the down counter 58 on the JAM signal. Upon the expiration of the minimum rate interval, the microprocessor is re-awakened to issue a stimulation pulse.

Any of several events can cause an interrupt request which restarts the microprocessor prematurely and causes it to branch out of the normal undisturbed pacer timing sequence of FIG. 2 and respond according to the type of interrupt.

If the pacer senses cardiac activity in the alert period, the microprocessor will be restarted with an interrupt request and the cardiac activity will by analyzed. In the case of a single R wave for example, (assuming a ventricular lead) in the alert period, the pacer timing cycle would be reinitialized by restarting the normal pacing cycle in the refractory period and, before turning off the microprocessor, loading a number into the down counter 58 sufficient to consume the entire refractory period as if a stimulation pulse had been issued. In the case of multiple R waves with an R to R interval less than the programmed tachycardia threshhold rate interval, the microprocessor, under software control, will go into any one of five antitachycardia modes. Programming, magnet and interrogate requests via reed switch 28 will also create an interrupt. The interrupt control logic 62 is nonresponsive, however, if the microprocessor is already running a given program segment. By software structure, reed switch interrupts are given priority over sense interrupts.

Whenever the microprocessor is re-awakened, the elapsed time is taken over the data bus from the up counter 56 via the tristate buffer 64 by the READ TIMER command. This operation enables the microprocessor to keep track of the elapsed time within a given cardiac cycle without remembering the preset number.

PACER OPERATION

Pacer operation is described in terms of the pulse to pulse interval. Each interval consists of programmable refractory and alert periods. In the refractory period, the pacer is non-responsive to cardiac activity. When the pacer is programmed to an asynchronous mode (VOO or AOO), the pacer remains refractory permanently and does not sense any cardiac signals. Pacing is always fixed at the programmed minimum rate in the asynchronous mode.

During the alert period, the pacer responds to cardiac activity as determined by the programmed mode. When the pacer is programmed to the VVI or AAI mode and cardiac activity is detected during the alert period, the pacer inhibits the output pulse (terminating the alert period) and starts a new interval. If cardiac activity is not detected by the end of the alert period, the pacer produces an output pulse. However, when the pacer is programmed to the VVT or AAT mode and cardiac activity or an external overdrive pulse is detected during the alert period, the pacer simultaneously produces an output pulse (terminating the alert period) and starts a new interval. The triggered output pulse has no physiological effect (except in overdrive mode) because it occurs during the heart's refractory period. However, the pulse is useful for diagnostic purposes. If cardiac activity is not detected by the end of the alert period, the pacer produces an output pulse.

The hysteresis pacing mode is designed to allow the patient to be supported by his or her own intrinsic heart rate for as long as possible. The heart's intrinsic beat is more efficient than a pacer induced beat. Thus, a given pacer rate would be equivalent in pumping capacity to a lower intrinsic rate. For example, say the pacer is programmed to VVI mode, 70 ppm rate and the hysteresis constant is 100 ms. The hysteresis rate therefore is 63 ppm (857 ms) (70 ppm)+100 ms=957 ms (63 ppm). If the patient's heart rate is 75 ppm and starts to slow down it would have to drop to 63 ppm before the pacer would take over and it would do so at its programmed rate of 70 ppm. If the patient's heart rate increased to 63 ppm the pacer would inhibit.

SOFTWARE

Except for the emergency VVI pacer (not used in this embodiment) and DMA RAM loading functions, the operation of the pacer of FIG. 1 is controlled in accordance with software instructions loaded into RAM 20. Software listings in hexidecimal code form and annotated assembly language from the standard instruction repertoire of the RCA 1802 microprocessor are stated in their entirety in the microfiche appendix, along with descriptions of module function and entry/exit conditions. The nomenclature "MA-5" means page 5 of the microfiche appendix. The I/O configuration and outputs are identified and described at MA-2 and 3. The register allocations for the microprocessor are given on MA-5 and 6. For example, one of the registers (RF) stores the programmed minimum rate interval code. This code represents the number of milliseconds from one ventricular stimulation pulse to the next in the asychronous mode or in the absence of cardiac activity in the inhibited mode. Other programmable parameters are stored in the microprocessor registers and in the current value array (CVA) in the RAM.

The software is stored in binary form in RAM 20 at addresses 0000 through 07FF beginning at MA-16. The last page, 0700-07FF, is used for variables such as the CVA and patient monitors. Once loaded, the remainder 0000-06FF acts like a ROM. The listings contained in the microfiche appendix are organized in modules corresponding to the software structure diagrams of FIGS. 18-26. A double line on the side of a block in FIGS. 19-24 represents a call to a subroutine.

The initialize routine represents the beginning point in the life of the cardiac pacer. Grounding the clear input to the microprocessor (LUMP pad 15, FIGS. 4A and 4B and 5) after the circuitry is powered up, automatically starts the microprocessor in the initialize routine (microfiche page MA-16) by zeroing the main program counter (register RO) and disabling the interrupt response capability.

Next, the microprocessor puts the entire RAM through checkerboard and inverse checkerboard tests to check memory function and to guard against coupling between adjacent memory cells. Failure stops the processor clock. Otherwise, the routine proceeds to telemeter each byte of memory (RAM 20) by pulse width modulation of the telemetry coils by the Q output of the microprocessor. The instruction to telemeter the next byte calls the telemetry subroutine. After telemetering out the entire memory contents for inspection, the program proceeds automatically to initialize the CPU registers with the STAT SET values (MA-18), e.g. setting the mode register (R5) to VVI, and entering the appropriate values in the current value array, a series of consecutive locations in RAM starting at 0700, MA-78. In addition, the arrhythmia counter is zeroed along with the patient monitor buffers. The input/output buffer register (RE,I/OBUF) is addressed to the hardware timer 55 (FIG. 6); the sensing routine program counter (R3, SNSPC) is pointed to the address of the sensing routine; and the pacer output subroutine selection register (R4) is stocked with the address of the main output subroutine. Next, the minimum rate interval register (RF) is loaded with 70 pulses per minute and the anode is set to ambipolar by latching the E line (I/O 1, FIGS. 4A and 4B). The ventricular sensitivity is set to 1½ millivolts by setting latches with the output lines G and H (I/O 3 and 4), whereupon the initialize routine is completed (MA-19).

The program jumps to INTRET (MA-66), a segment of the programming interrupt routine (namely, programming interrupt return module, MA-66) which initializes the addressing of the remaining registers and waits for the pacer timer clock flag (EF1 to synchronize the pacer timing, loads charge dump interval into timer, blanks the sense amplifier, and returns to the main pacing routine at RETPROG (MA-29) via the sensing routine entry module.

In the main pacing routine, the microprocessor calls the output subroutine which has been initialized at the main output subroutine (MA-49). This subroutine calls the average rate subroutine, following which the microprocessor returns to the calling module, namely the pacing routine immediately following the RETPROG step. The I/O buffer register is initialized for a charge dump and the real time subroutine is called before stopping the microprocessor clock via the halt command.

To summarize the operation up to this point, the pacer begins up in the initialize mode where it checks the RAM, loads STAT SET parameters into registers and loads addresses of the first used subroutines, executes a return to the main pacing routine, just as if it were returning from a programming interrupt, updates the REAL time counter, sets the pacer timer 55 and stops the microprocessor clock. During execution of the programming interrupt return module, (INTRET), the charge dump time was loaded into the timer off the address bus. Thus, by the time the HALT command occurs, the pacer timer 55 has just started counting down the charge dump period.

When the timer times out, the zero detect output of the down counter 58 (FIG. 6) reactivates the microprocessor clock 60. The program resumes at the END CHARGE DUMP module (MA-30).

The microprocessor terminates the charge dump by outputting data to the latch to open the correct transmission gate on the I/O hybrid. Next, the programmed refractory period is loaded and compared to the minimum rate interval. If the refractory period is somehow longer than the minimum rate interval, the pacer timer is set to an interval corresponding to the minimum rate interval, less the already expired charged dump and the routine skips the ending of the refractory period and goes directly to the output next module (MA-25) and stops the processor clock to await an interrupt or expiration of the minimum rate interval. If the refractory period is less than the minimum rate interval the pacer timer is set to refractory period less the elapsed charge dump time and the processor clock is stopped. At the end of the refractory period the microprocessor is awakened to update the VTIME and enable sensing. The VTIME register keeps track of time since the last ventricular event (or atrial depending on lead location). Finally, the pacer timer is set to the value of the temporary register, which holds the minimum rate interval, less the elapsed refractory time. The program then branches to the OUTNXT location (MA-25) at which the correct refractory period for the next output pulse is loaded and the microprocessor clock is stopped while the pacer timer times the alert period.

If the alert period elapses without an interrupt, the timer 55 reawakens the microprocessor at the top of the pacer output routine. The time since the last ventricular event is calculated and the arrhythmia counter is decremented. If the ventricular output is OFF, the microprocessor branches to the OUTPUT OFF point in the pacing routine. In normal operation with the ventricular output ON, the pacer output routine disables the sense amplifier, increments the paced event counter, checks for runaway (timer clock check module), sets the pacer timer to the charge dump interval, decrements the arrhythmia counter issues an output pulse, starts the charge dump, updates the average rate and real time counter and stops the processor clock.

Runaway detection is executed in software by timing the timer clock interval at EF1 with a timing loop. If the clock interval exceeds a predetermined number by 14%, the pacer executes a fail-safe mode by self-programming the minimum rate to OFF and disabling the pacer output. The OFF rate actually corresponds to 30 mmp—the maximum time interval and lowest power mode. Although disabled, the pacer can be reprogrammed to a new minimum rate. However, unless runaway detection was a fluke caused by noise, the pacer will reprogram itself OFF before the next output pulse.

The foregoing operation will continue indefinitely in the absense of an interrupt. Note that during the alert period and refractory period, the microprocessor clock is stopped and the hardware pacer timer 55 is keeping track of elapsed time as well as counting down from the preset.

If there is sensed cardiac activity during the alert period while the microprocessor is stopped, the I/O hybrid 12 produces a VSENS logic output which is passed to the to the LUMP circuit (SENS 2)-bar as an input to the interrupt control logic 62 (FIG. 6). Interrupt control logic 62 restarts the microprocessor clock 60 so that the microprocessor can field an interrupt request. The microprocessor calls the interrupt service routine entry point (MA-68). In the absence of a reed switch closure (EF2), the program knows that the interrupt was caused by VSENS and branches to the return location where the sensing routine counter is designated the program counter. During the initialization routine, the sensing routine program counter was loaded with the address SENSROUT, thus when returning from a sense interrupt, the sensing routine is entered at that point (MA-36). Once inside the sensing routine, after disabling further sensing, the microprocessor waits for the falling edge of the next pulse (EF1) to synchronize the microprocessor with the pacer timer 55. The time is then added to VTIME and unless a magnet is present, the tachycardia monitor subroutine is executed. The operation returns to the departure point in the sensing routine and sets up a return to sense blanking unless in the triggered mode (in which case the return is set up for PACERTRIG). Before returning to the main program counter, the arrhythmia counter is decremented and the sensed event counter is incremented.

The remaining routines or modules for programming and magnet interrupts, tachycardia recognition, automatic antitachycardia outputs and updating the patient monitor are described in detail in the microfiche appendix.

OPERATION

The pacer has three basic pacing modes—asynchronous, inhibited or triggered—to which it can be programmed. An automatic antitachycardia mechanism can also be selected. The pacer's working definition of tachycardia is a persistent atrial or venticular (depending on lead location) heart rate greater than the programmed tachycardia threshold rate. Should the pacer detect a tachycardia, it will initiate the preprogrammed automatic antitachycardia mechanism. When the tachycardia is terminated, the pacer will revert to its normal pacing mode at the programmed minimum rate. The minimum rate can also be programmed OFF to limit the pacer's function to only monitoring and responding to tachycardias.

TACHYCARDIA DETECTION

The pacer of the present embodiment has a programmable tachycardia threshold rate of 100–220 ppm (600 ms–273 ms intervals). Tachycardia detection is based on the number of times the rate threshold is exceeded before reverting to a normal cardiac cycle. To keep track of this number, an arrhythmia counter is established. The counter is initially set to zero and increments by one whenever it detects an intrinsic pulse to pulse interval shorter than the programmed tachycardia threshold rate. The arrhythmia counter is decremented by one whenever it detects an interval greater than the threshold interval, e.g., a normal cardiac cycle. The count threshold number which triggers the antitachycardia mechanism is programmable. This count also determines the number of intrinsic intervals between termination attempts for each tachycardia episode. A programmable maximum number of termination attempts is allowed. If the maximum number of "tries" are made, further termination attempts cease and the pacer reverts to the inhibited pacing mode. The maximum number of attempts is reset upon termination of the tachycardia, application and removal of the magnet or by any programming operation.

Assume the threshold is 6, for example. Five consecutive tachycardias (intervals less than threshold), followed by two consecutive normal spontaneous or paced intervals would result in the counter being incremented to 5 and decremented back down to 3. Three additional consecutive tachycardias will boost the count to 6 which causes the pacer to abandon the normal pacing mode and immediately enter the programmed antitachycardia mechanism. Following application of the ATM, the arrhythmia counter is set to 3. This is done so that three non-tachycardia pacer cycles will cause exit from the tachycardia response mode. To initiate another termination attempt (after the first) the arrhythmia counter must reach 9, i.e., the programmed recognition count plus 3.

PROGRAMMABLE AUTOMATIC ANTITACHYCARDIA MECHANISMS

Five antitachycardia mechanisms are available for programmable selection by the physician. By observation of the patient and analysis of the data returned by the embedded patient monitor system (described below), the physician can selectively examine the chronic benefits for the patient of any one of the five antitachycardia mechanisms. Each mechanism has a set of programmable parameters which allow the physician to customize the treatment. These parameters are shown in paragraph 10 of Table III, above. The operation of the specific antitachycardia mechanism is illustrated by the EKG traces in FIGS. 12–16.

1. Programmed Burst (FIG. 12)

When the pacer is programmed for the programmed burst antitachycardia mechanism and a tachycardia is detected, the pacer responds with a burst of a predetermined number of pulses (up to 30) at a preprogrammed rate. This rate can be fixed, automatically incremented, or automatically decremented with each pulse in the burst.

EXAMPLE

The pacer is programmed to the following values (see Table III):

| | |
|---|---|
| Tachycardia threshold rate | 100 ppm (600 ms) |
| Burst rate | 200 ppm (300 ms) |
| Number of pulses in burst | 7 |
| Ramp steps | +31 ms |
| Termination attempts | infinity |
| Tachycardia recognition count | 6 |

If the pacer detects six consecutive intrinsic intervals less than 600 ms (interval corresponding to the tachycardia threshold rate), the pacer outputs a pulse 300 ms (burst rate) after the sixth intrinsic interval.

Each paced interval that follows increases by 31 ms (ramp step) until seven pulses (number of pulses in burst) have been delivered (FIG. 12). The final paced interval in the sequence is 486 ms long [(300 ms)+(6×31 ms)]=486 ms.

If the tachycardia is not terminated and the pacer detects another six consecutive intrinsic intervals which are less than 600 ms (interval corresponding to the tachycardia recognition rate) the burst sequence is repeated. When the tachycardia is terminated or the programmed maximum number of termination attempts is completed, the pacer returns to the previously programmed mode and parameter values.

2. Burst Rate Scanning (FIG. 13)

The burst scanning mechanism is identical to the programmed burst mechanism, with one exception. If the first burst sequence does not terminate the tachycardia, the burst rate used in the following sequence is adjusted to the value of the programmed scan delta. This adjustment continues until the programmed maximum burst rate is reached, the tachycardia is terminated, or the programmed number of termination attempts is completed. If the maximum burst rate is reached, the burst rate is set at the programmed minimum burst rate and successively increased by the scan delta until the tachycardia is terminated or the programmed number of termination attempts is completed. The burst rate value that terminates the tachycardia is stored in pacer memory as the "present burst rate" and is the first value tried when the next tachycardia is detected. If the sequence stops due to the completion of the programmed number of termination attempts, the first value used during the next tachycardia episode will be the next value in the sequence.

EXAMPLE

The pacer is programmed to the following values:

| | |
|---|---|
| Maximum burst rate | 300 ppm (200 ms) |
| Minimum burst rate | 167 ppm (360 ms) |
| Present burst rate | 230 ppm (260 ms) |
| Tachycardia threshold rate | 100 ppm (600 ms) |
| Scan delta | −31 ms |
| Number of pulses in burst | 7 |
| Ramp steps | 0 |
| Termination attempts | infinity |
| Tachycardia recognition count | 6 |

If the pacer detects six consecutive intrinsic intervals less than 600 ms (interval corresponding to the tachycardia threshold rate), the pacer issues an output pulse 260 ms (present burst rate) after the sixth interval (FIG. 13A). Because the ramp step is programmed to zero, the pacer maintains the present burst rate for seven pulses (number of pulses in burst).

If the tachycardia is not terminated and the pacer detects another six consecutive intrinsic intervals less than 600 ms, the burst sequence is repeated at a burst rate of 262 ppm [260 ms (present burst rate)−31 ms (scan delta)=229 ms (262 ppm)]. See FIG. 13B.

The burst sequence continues until the tachycardia is terminated, or until the present burst rate equals 300 ppm (maximum burst rate). If the present burst rate reaches 300 ppm, it is set to 170 ppm (minimum burst rate). The burst rate interval is successively decreased by 31 ms (scan delta) for each burst sequence, until the tachycardia is terminated. The burst rate value which terminates the tachycardia is stored in pacer memory and is the first value tried when the next tachycardia is detected.

3. Automatic Overdrive (FIG. 14)

When the pacer is programmed to the automatic overdrive mechanism, and a tachycardia is detected by the pacer, it measures the tachycardia rate (running average of four intervals), and responds with a burst rate faster than the measured tachycardia rate. This ATM is thus a function of the patient's intrinsic rate in tachycardia.

EXAMPLE

The pacer is programmed to the following values:

| | |
|---|---|
| Tachycardia threshold rate | 100 ppm (600 ms) |
| Overdrive constant | 100 ms |
| Number of pulses in burst | 7 |
| Ramp steps | 0 |
| Maximum overdrive rate | 300 ppm (200 ms) |
| Termination attempts | infinity |
| Tachycardia recognition count | 6 |

The pacer detects a tachycardia and measures the tachycardia rate at 107 ppm (560 ms). A burst rate of 130 ppm [560 ms (tachycardia rate)−100 ms (overdrive constant)=460 ms (130 ppm)] is initiated by the pacer (FIG. 14). Because the ramp step is programmed to zero, the pacer maintains the burst rate for 7 pulses (number of pulses in burst). If the tachycardia is not terminated, the pacer repeats the burst rate sequence. After the first attempt to terminate the tachycardia, the burst rate may change, depending on the measured tachycardia rate in the interim. However, the burst rate will not exceed the programmed maximum overdrive rate.

4. Programmed Critically Timed (FIG. 15)

When the pacer is programmed to the programmed critically timed mechanism and a tachycardia is detected, the pacer responds with a sequence of three critically-timed pulses (S1, S2, S3).

EXAMPLE

The pacer is programmed to the following values:

| | |
|---|---|
| S1 (first critically timed interval) | 360 ms |
| S2 (second critically timed interval) | 300 ms |
| S3 (third critically timed interval) | 260 ms |
| Tachycardia threshold rate | 100 ppm (600 ms) |
| Termination attempts | infinity |
| Tachycardia recognition count | 6 |

When the pacer detects a tachycardia, the first pulse (S1) is issued 360 ms after the sixth consecutive intrinsic interval less than 600 ms (interval corresponding to the tachycardia threshold rate). The second pulse (S2) is issued 300 ms after S1 and the third pulse (S3) 260 ms after S2 (FIG. 15). If the tachycardia is not terminated and another six consecutive intrinsic intervals less than 600 ms are detected, the sequence of critically timed pulses is repeated until the tachycardia is terminated or the programmed number of termination attempts is completed.

5. Critically Timed Scanning (FIG. 16)

When the pacer is programmed to the critically timed scanning mechanism and a tachycardia is detected, the pacer outputs a single premature pulse (S1). If the tachycardia is not terminated and the programmed tachycardia recognition count (plus 3) is attained, the pacer outputs a pair of pulses (S1 and S2).

After each attempt to terminate the tachycardia, S2 is decreased by the scan delta until S2 reaches the minimum premature interval (S Min.). Then, S1 is decreased by the scan delta and S2 is set equal to S1. S1 is tried alone before resuming S2 scanning. S1 is decreased by the scan delta and tried alone whenever S2 reaches the programmed minimum interval. The pacer outputs the S1 pulse until it reaches S Min. If S1 reaches S Min. before the tachycardia is terminated, S1 and S2 are set equal to the maximum premature interval (S Max.) and the sequence continues.

The values of S1 and S2 that terminate the tachycardia are stored in pacer memory and are the initial values tried during the next tachycardia. If the sequence stops due to the completion of the programmed number of termination attempts, the first value used during the next tachycardia episode will be the next value in the sequence.

EXAMPLE

The pacer is programmed to the following values:

| | |
|---|---|
| S1 (present value) | 340 ms |
| S2 (present value) | 260 ms |
| S Min. (minimum premature interval) | 220 ms |
| S Max. (maximum premature interval) | 360 ms |
| Scan delta | −31 ms |
| Tachycardia threshold rate | 100 ppm (600 ms) |
| Termination attempts | infinity |
| Tachycardia recognition count | 6 |

When the pacer detects six consecutive intrinsic intervals less than 600 ms (interval corresponding to the tachycardia threshold rate), a pulse (S1) is issued 340 ms after the last interval. If six additional consecutive intrinsic intervals less than 600 ms are detected, the pacer issues one pulse (S1) 340 ms after the last interval, and another pulse (S2) 260 ms after S1 (FIG. 16). S2 is decreased by 31 ms (scan delta).

If the tachycardia is not terminated, the pacer issues a pulse 340 ms (S1) after the sixth interval and another pulse 229 ms (S2=260 ms−31 ms) after S1. S2 is again decreased by 31 ms. S2 (198 ms) is now equal to or less than 220 ms (S Min.). Therefore, S1 is set to 309 ms (340 ms−31 ms), and S2 is set to 309 ms (S2=S1).

If the tachycardia continues, the pacer issues a pulse 309 ms (S1) after the sixth interval. If six additional intervals are detected, the pacer issues a pulse 309 ms (S1) after the last interval and a second pulse 309 ms (S2) after S1. S2 is then decreased by 31 ms.

If the tachycardia persists, the pacer continues to issue S1 and S2 pulses. S2 is decreased by 31 ms until S2 is equal to or less than 220 ms (S Min.). Then S1 is set to 278 ms (309 ms−31 ms) and S2 is set equal to S1.

The pacer issues an S1 pulse, and then S1 and S2 pulses until S2 reaches 220 ms or less (S Min.) This sequence continues until the tachycardia is terminated or until S1 reaches S Min. Then S1 and S2 are set to 360 ms (S Max.) and the sequence continues. The values of S1 and S2 that terminate the tachycardia are stored in pacer memory and used as the starting point for S1 and S2 values when another tachycardia is detected.

PROGRAMMING AND TELEMETRY

External pacer programming is accomplished via the reed switch 28 (FIGS. 1 and 5) inside the pacer. Information is transmitted in serial binary form by pulse width modulation of the external programming electromagnet. In order to reprogram the pacer, a program access code consisting of a synchronizing pulse and a 5 bit ID code must precede any programming.

After receiving the program access code, the pacer telemeters via the telemetry drivers Q2 and Q3 and coils L1 and L2 (FIG. 4, 5), a 2-byte pacer serial number and a 2-byte model number. Next the programmer transmits a number o f 16 bit strings (up to 23) depending on the number of parameters being programmed at one time. Each string is divided into 8 bits of program code and 8 bits of parameter code. The program code identifies the parameter to be changed, i.e., minimum rate, refractory period, pacing mode, etc. The parameter code identifies the desired value for the given parameter, e.g., a minimum rate of 70 ppm. Following transmission of the 16 bit programming strings, the pacer will automatically telemeter back (echo back module) each of the programming strings received by the pacer on a first in first out basis.

After the programmer verifies the information transmitted by the pacer, it will issue one of two 3 bit activate commands. The pacer will then implement its programmed parameters and, depending on the activate command selected, will telemeter one of two sequences:

Activate Command No. 1: Upon reception, the pacer will implement programming and then issue a "verify" pulse to acknowledge activation of the desired parameters in the pacer;

Activate Command No. 2: Upon reception, the pacer implements programming and then issues a verify pulse followed by telemetry of the 24 byte current value array (CVA). The CVA is the RAM location containing all of the programmed parameters.

The pacer of the present emodiment is designed not only to be programmed externally but also to be interrogated to command the pacer to transmit specific information via telemetry. If an interrogate request code is sent to the pacer, the microprocessor immediately interrupts its normal pacing sequence, issues a 750 microsecond verify pulse followed by a 2 ms pause and telemeters the requested information.

The last page of pacer memory (RAM 20) stores three different types of data as shown in the table below.

TABLE IV
Categories of RAM Data for Telemetry

1. Programmed parameter values (CVA).
2. Patient monitored data.
    A. Short-term monitored pacing data (programmable duration).
        (1) Percent sensing.
        (2) Average rate.
        (3) Maximum rate.
        (4) Number of tachycardia episodes.
        (5) Maximum tachycardia duration.
    B. Long-term monitored pacing data.
        (1) Number of days since last follow-up.
        (2) Percent sensing.
        (3) Average rate.
        (4) Maximum rate.
        (5) Number of tachycardia episodes.
        (6) Maximum tachycardia duration.
3. Stored information.
    A. Manufacturing data.
        (1) Serial number of pacer.
        (2) Model number of pacer.
    B. Implant Data.
        (1) Number of days since implantation.
        (2) Lead/Electrode information.
    C. Patient data. (See Table V.)

Programmed parameter values are stored in the CVA block of RAM. The monitored data is stored in the monitor buffer. This data is entered and updated automatically by the pacer while it is being worn by the patient. The short-term monitored pacing data buffer is stored in RAM and contains pacing data from the last 12 blocks of programmable duration. The real time counter (MA-81) is employed to "shift each block out after 1/12 of the duration elapses. The real time subroutine (MA-59) is called once per pacer cycle by either a sensed or paced event. The real timer operates as a many stage counter which is updated by VTIME at the end of every pacer cycle. Tachycardia duration is measured by a special counter that is updated by the real time counter chain only in the presence of tachycardia. If the address in the pacer output subroutine pointer (OUTSUB) is higher than that of the main output subroutine, tachycardia is deemed present. Stored information, like parameter values is data which is entered by the factory or physician at the time of programming. It also consists of data wich can be entered from time to time by the physician to update the patient's history. Typical information is shown in Table V below.

TABLE V

| I | Patient Identification |
| | Three Letters and Birthdate YY-MM-DD |
| II. | Lead Information |
| | Type |
| | Manufacturer |
| | Serial Number |
| | Placement |
| III. | Implant Date |
| | Pacer |
| | Lead |
| IV. | Pre-Implant Symptoms |
| | 1. Unspecified |
| | 2. Uncoded |
| | 3. Snycope |

TABLE V-continued

|  |  |
| --- | --- |
|  | 4. Dizzy Spells |
|  | 5. Bradycardia |
|  | 6. Tachycardia |
|  | 7. Prophylactic |
|  | 8. Heart Failure |
|  | 9. Cerebral Dysfunction |
| V. | Pre-Pacing ECG |
|  | 1. Rhythm Unspecified |
|  | 2. Rhythm Uncoded |
|  | 3. Normal Sinus Rhythm |
|  | 4. 1' Heart Block |
|  | 5. 2' Heart Block - Unspecified |
|  | 6. 2' Heart Block - Wenckebach |
|  | 7. 2' Heart Block - Mobitz |
|  | 8. CHB - QRS Unspecified |
|  | 9. CHB - Narrow QRS |
|  | 10. CHG - Wide QRS |
|  | 11. Bundle Branch Block - Unspecified |
|  | 12. RBBB - Incomplete |
|  | 13. RBBB - Complete |
|  | 14. LBBB - Complete |
|  | 15. Left Anterior Hemiblock |
|  | 16. Left Posterior Hemiblock |
|  | 17. RBBB + LAHB + Normal PR |
|  | 18. RBBB + LPHB + Normal PR |
|  | 19. RBBB + LAHB + Long PR Interval |
|  | 20. RBBB + LPHB + Long PR Interval |
|  | 21. LBBB + Long PR Interval |
|  | 22. SSS - Unspecified |
|  | 23. SSS - SA Exit Block |
|  | 24. SSS - SA Arrest |
|  | 25. SSS - Bradycardia |
|  | 26. SSS - Brady-Tachy |
|  | 27. SSS + AV Block |
|  | 28. Ventricular Extrasystoles |
|  | 29. Ventricular Tachycardia |
|  | 30. Paroxysmal VF |
|  | 31. A Flutter/FIB + Bradycardia |
|  | 32. Atrial Tachycardia |
|  | 33. Pre-Excitation |
| VI | Etiology |
|  | 1. Etiology Unspecified |
|  | 2. Etiology Uncoded |
|  | 3. Etiology Unknown |
|  | 4. Conduction Tissue Fibrosis |
|  | 5. Ischemic |
|  | 6. Post-Infarction |
|  | 7. Surgical |
|  | 8. Congenital |
|  | 9. Cardiomyopathy |
|  | 10. Myocarditis |
|  | 11. Valvular Heart Disease |
|  | 12. Carotid Sinus Syndrome |
| VII. | Drug Therapy |
|  | 1. None |
|  | 2. Unspecified |
|  | 3. Uncoded |
|  | 4. Anticholinergics |
|  | 5. Digitalis Preparations |
|  | 6. Diuretics |
|  | 7. Potassium |
|  | 8. B Blockers |
|  | 9. CA Blockers |
|  | 10. Other Antiarrhythmic Agents |
|  | 11. Anticoagulant/Antiplatelet Agents |
|  | 12. Coronary Vasodilators |
|  | 13. Other |
| VIII. | Capture |
|  | 1. Atrial |
|  |    Voltage - Current - Pulse Width |
|  |    Impedance |
|  |    Polarity |
|  | 2. Ventricular |
|  |    Voltage - Current - Pulse Width |
|  |    Impedance |
|  |    Polarity |
| IX. | Sensing Tresholds at Implant |
|  | P Wave Amplitude |
|  | R Wave Amplitude |
| X. | Retrograde Conduction |
|  | Present or Absent |

TABLE V-continued
Time in MSEC

Stored data is entered by the programmer in the same manner as parameters.

The program code byte addresses the stored data location. After entering the data, the pacer automatically echoes back the received data for comparison just as in the programming of pacer parameters.

Four interrogate requests are possible. Calling for "interrogate CVA" causes the pacer to telemeter 24 bytes containing the software release number and 23 bytes of CVA not monitored dta.

Calling for "monitor buffer", causes the pacer to telemeter 112 bytes consisting of patient monitored data such as percent pacing, average rate, etc. A "RAM dump" command followed by a line number, requests the pacer to telemeter the entire contents of RAM starting from the designated RAM location. A maximum of 2K bytes can be telemetered starting from address 0000. Asking for "all dump", commands the pacer to telemeter all of the information in Table IV, that is, the CV, monitored data and stored data.

The telemetered data is received by the external programmer (not shown), buffered into external memory and displayed by a CRT or printer driven by the external programmer.

The interrogation and telemetry functions provide a programming security system. This system includes automatic programmer lockouts, which prevent the transmission of inappropriate programming combinations, and input verifications intended to protect against inadvertent selections of certain critical parameters.

Certain parameter value combinations can be harmful to the patient. If these combinations are selected, they should be automatically locked out or disabled by the programmer. Ideally when a lockout is in effect and programming of the indicated parameters is prevented, an explanation will appear on the programmer's display.

The following rules must be observed when selecting parameter values. If they are not observed, an automatic programmer lockout should occur:
1. Minimum rate must be less than tachycardia recognition rate.
2. Refractory period plus 25 ms must be less than or equal to the interval of the tachycardia recognition rate or the pacer cannot detect tachycardias.
3. When unipolar lead information has been programmed into pacer memory, changing polarity to bipolar is locked out. If this programming transmission were allowed, there would be no pacer output. With a bipolar lead, the polarity must be bipolar or ambipolar. However, the case connections are identical for unipolar and ambipolar (see FIG. 3).

When selecting parameter values for the ATM, the following rules should be observed:
1. Programmed burst mechanism—if the ramp step is negative, the final interval must not be less than 150 ms or 60 ms for ventricular or atrial lead locations, respectively.
2. Burst rate scanning mechanism
   A. Minimum burst rate must be less than or equal to the present burst rate.
   B. Present burst rate must be less than or equal to the maximum burst rate.
   C. If the ramp step is negative, the final interval must not be less than 150 ms or 60 ms for ventricular or atrial lead location, respectively.
3. Critically timed scanning mechanism
   A. Minimum premature interval must be less than or equal to the maximum premature interval.
   B. Minimum premature interval must be less than or equal to S1.
   C. S2 must be less than or equal to the maximum premature interval.

In addition to observing the above conditions, input verifications should be incorporated in the program to alert the programmer to critical parameters to avoid inadvertent programming selections. For example, when such a selection is made, the programmer can display a inquiry requiring a yes answer before the selection will be transmitted. The following programming selections should be verified before programming is possible:
1. Minimum rate OFF
2. Antitachycardia mechanism OFF
3. Refractory period of 150, 200 or 250 ms.
4. VOO mode—if an antitachycardia mechanism is programmed and change to VOO mode is proposed, the programmer should display a message reminding the programmer that tachycardia detection will not be possible since the sense amplifier is disabled.

FEATURES AND ADVANTAGES

The advantages of the novel pacer design described above are numerous. Because of the intermittent operation of the microprocessor and the extensive use of CMOS circuitry including RC clock circuits, the current drain is kept exceedingly low, extending the battery life of the pacer, while offering software control of all pacer functions in a multiprogrammable cardiac pacer with telemetry comparable in size to the smallest full function cardiac pacers on the market today. The selectable antitachycardia mechanism provide the physician with an arsenal of techniques to counteract tachycardia. Each technique can be tailored specifically to the patient's condition. By electrophysiological evaluation the physician can refine the tachycardia respose mode identify the single most effective strategy in breaking tachycardias in a given patient. The detection criteria for entering the antitachycardia mode and the number of unsuccessful tries before forced exiting of antitachycardia mode are also made programmable.

Outbound telemetry is expanded to include not only parameter values and implant information, but also the relevant medical history of the patient can be entered and updated by the physician. The pacer is enabled to create its own history by collecting and organizing patient monitored data. By observing the number of tachycardias in a programmed block of time, the physician can observe how well the antitachycardia mechanism is working as well as the patient's current pacer-dependency.

The present embodiment is believed to be the first complete implementation of a ROM-less computerized pacer. That is, all software is stored in volatile memory (RAM). This technique allows maximum flexibility by making all aspects of the software factory loadable without waiting to mask new ROM's to change the software. If desired, as shown in FIG. 12, a small portion of the RAM can be dedicated to an operating system which will enable new software to be down loaded by the external programmer.

Many variations and modifications of the foregoing specific embodiment are, of course, possible without departing from the spirit and scope of the invention. For example, there are doubtless other ways of implementing the pacer timer 55 without using the same arrangement of up and down counters. The emergency VVI pacer can be implemented as shown along with the 32 kHz crystal, if desired. In any event, the specific embodiment is intended only to be illustrative and not restrictive as to the scope of the invention, which is indicated by the appended claims and equivalents thereto.

What is claimed is

1. An implantable computer-based cardiac pacer comprising
   at least one pacer terminal,
   output means for issuing an output via said terminal in response to an output command,
   a computer including digital storage with stored program means for defining a series of instructions and processing means for fetching and executing said instructions,
   said stored program means including means defining a main pacing routine for issuing an output command in accordance with internal timing logic,
   clock means connected to said processing means for running said computer means,
   presettable timer means clockwise independent of said computer for receiving a preset number from said computer and for producing a zero output at the end of the time period corresponding to said present number,
   said stored program means further including means for loading said timer means with a preset number and then issuing a halt command,
   clock control means responsive to said halt command for disabling the clock means output for stopping said computer and responsive to either the zero output of said timer means or to a signal originating externally of said pacer for enabling said clock means to restart said computer,
   said timer means including a presettable down counter producing said zero output and an up counter and means for presetting and enabling said down counter substantially simultaneously with resetting said counter, and
   parallel bus means for connecting the present input of said down counter and a set of parallel outputs of said up counter to said computer to transfer parallel binary numbers from said computer to said down counter and from said up counter to said computer on command.

2. An implantable electronic biomedical device for monitoring bio-electrical activity, comprising
   a terminal for connection to electrically active tissue,
   a CPU for executing stored instructions,
   a CPU clock disabled by a halt command from said CPU,
   a timer clockwise independent of said CPU,
   means arising from instruction execution by said CPU for presetting said timer to a variable time interval and issuing a half command,
   means responsive to the timing out of said timer for restarting said CPU clock,
   means response to electrical activity at said terminal for restarting said CPU clock and issuing an interrupt request for said CPU,
   means for keeping track of the elapsed time while said CPU clock is OFF, and
   means responsive to the timing out of said timer for disabling said interrupt request means.

3. The device of claim 2, further comprising
   means responsive to the timing out of said timer for disabling said interrupt request means.

4. The device of claim 2, further comprising
   means responsive to an externally generated communication for restarting said CPU clock and issuing an interrupt request to said CPU.

5. The device of claim 4, further comprising means for giving interrupt priority to said communication.

6. The stimulator of claim 5, further comprising
   means responsive to an externally generated communication for restarting said CPU lock and issuing an interrupt request to said CPU.

7. The stimulator of claim 5, further comprising
   means for giving interrupt priority to said communication.

8. An implantable tissue stimulator, comprising
   a terminal for connection to electrically active tissue,
   a CPU for executing stored instructions.
   a CPU clock disabled by a halt command from said CPU,
   a timer clockwise independent of said CPU,
   means arising from instruction execution by said CPU for presetting said timer to a variable timer interval and issuing a halt command,
   means responsive to the timing out of said timer for restarting said CPU clock,
   means arising from instruction execution for causing said CPU to issue an output command according to a predetermined schedule,
   means responsive to a CPU output command for applying electrical stimulation via said terminal,
   means for keeping track of the elapsed time while said CPU clock is OFF,
   means responsive to spontaneous electrical activity at said terminal for restarting said CPU clock and issuing an interrupt request to said CPU, and
   means responsive to the timing out of said timer for disabling said interrupt request means.

9. The stimulator of claim 8, further comprising
   means responsive to spontaneous electrical activity at said terminal for restarting said CPU clock and issuing an interrupt request to said CPU.

10. The stimulator of claim 9, further comprising
    means responsive to the timing out of said timer for disabling said interrupt request means.

11. An implantable cardiac pacer, comprising
    an electrical terminal for connection to cardiac tissue,
    sensing means connected to said terminal for producing a sense output indicative of cardiac activity,
    a CPU for executing stored instructions,
    a CPU clock disabled by a halt command,
    a presettable pacer timer clockwise independent of said CPU having a preset input intercommunicated with said CPU,
    means arising from instruction execution by said CPU for loading a number indicative of a variable time interval via the present input to said pacer timer and for issuing a halt command to stop said CPU clock, means for determining the correct number to load into said pacer timer to time respective different portions of a predetermined pacer cycle, means defining corresponding tasks to be performed by the CPU upon restarting of said CPU clock, depending upon the point within the pacer cycle at which said CPU clock is restarted, means responsive to the timing out of said pacer timer for re-enabling said CPU clock, means responsive to said sense output for re-enabling said CPU clock and issuing an interrupt request to said CPU, means for keeping track of the elapsed time while said CPU clock is OFF;

output means for applying an electrical stimulation pulse via said terminal in response to an output command from said CPU, means arising from instruction execution by said CPU for disabling said sensing means, issuing an output command and loading a number into the timer via the preset input equivalent to at least a portion of the remainder of the refractory period and issuing a halt command to stop the CPU clock, means arising from instruction execution by said CPU upon the restarting of the CPU clock after timing out of said pacer timer for terminating the refractory period by enabling said sensing means, loading a number equivalent to the remainder of a minimum rate interval into said pacer time via the preset input and issuing a half command to stop the CPU clock, real time clock register accessible to said CPU, and means for incrementing said real time clock register while the CPU is running and for adding to said real time clock register said elapsed time after the CPU clock is restarted.

12. The cardiac pacer of claim 11, wherein said logic means further includes means responsive to restarting of the CPU clock by the occurrence of either a sensed output or the timing out of the minimum rate interval by the pacer timer in an alert period for resetting the pacer cycle timing.

13. An implantable cardiac pacer, comprising an electrical terminal for connection to cardiac tissue, sensing means connected to said terminal for producing a sense output indicative of cardiac activity, a CPU for executing stored instructions, a CPU clock disabled by a halt command, a presettable pacer timer clockwise independent of said CPU having a preset enable input intercommunicated with said CPU, means arising from instruction execution by said CPU for loading a number indicative of a variable time interval via the preset input to said pacer timer and for issuing a halt command to stop said CPU clock, means for determining the correct number to load into said pacer timer to time respective different portions of a predetermined pacer cycle, means defining corresponding tasks to be performed by the CPU upon restarting of said CPU clock, depending upon the point within the pacer cycle at which said CPU clock is restarted, means responsive to the timing out of said pacer timer for re-enabling said CPU clock, means responsive to said sense output for re-enabling said CPU clock and issuing an interrupt request to said CPU, means for keeping track of the elapsed time while said CPU clock is OFF;

output means for applying an electrical stimulation pulse via said terminal in response to an output command from said CPU, means arising from instruction execution by said CPU for disabling said sensing means, issuing an output command and loading a number into the timer via the preset input equivalent to at least a portion of the remainder of the refractory period and issuing a halt command to stop the CPU clock, means arising from instruction execution by said CPU upon the restarting of the CPU clock after timing out of said pacer timer for terminating the refractory period by enabling said sending means, loading a number equivalent to the remainder of a minimum rate interval into said pacer timer via the preset input and issuing a halt command to stop the CPU clock, charge dump means responsive to commands from said CPU for removing residual charge remaining on the terminal after a stimulation output, means arising from instruction execution from issuing a begin charge dump command by said CPU after a stimulation output command, loading a preset number into said pacer timer equivalent to the remainder of a charge dump period and issuing a halt command to stop the CPU clock, means arising from instruction execution following the re-enabling of the CPU clock at the end of the charge dump period for terminating charge dumping by issuing an end charge dump command, loading a new preset number into said pacer timer equivalent to the remainder of the refractory period, followed by a halt command to stop the CPU clock.

* * * * *